United States Patent
Gilbert et al.

(10) Patent No.: US 7,795,270 B2
(45) Date of Patent: Sep. 14, 2010

(54) DUTPASE INHIBITORS

(75) Inventors: Ian Gilbert, Dundee (GB); Corinne Nguyen, Cardiff (GB); Gian Filippo Ruda, Dundee (GB); Alessandro Schipani, Dundee (GB); Ganasan Kasinathan, Cardiff (GB); Nils-Gunnar Johansson, Enhörna (SE); Dolores Gonzalez Pacanowska, Granada (ES)

(73) Assignee: Medivir AB, Huddinge (SE)

( * ) Notice: Subject to any disclaimer, the term of this patent is extended or adjusted under 35 U.S.C. 154(b) by 935 days.

(21) Appl. No.: 10/585,283

(22) PCT Filed: Jan. 6, 2005

(86) PCT No.: PCT/GB2005/050002

§ 371 (c)(1),
(2), (4) Date: Oct. 2, 2006

(87) PCT Pub. No.: WO2005/065689

PCT Pub. Date: Jul. 21, 2005

(65) Prior Publication Data

US 2008/0312183 A1     Dec. 18, 2008

(30) Foreign Application Priority Data

Jan. 8, 2004    (GB) .................. 0400290.3

(51) Int. Cl.
*A61K 31/505* (2006.01)
*C07D 239/54* (2006.01)
(52) U.S. Cl. .................. 514/269; 544/309; 544/311
(58) Field of Classification Search ............ 544/309, 544/311; 514/269
See application file for complete search history.

(56) References Cited

U.S. PATENT DOCUMENTS

| 5,859,014 A | 1/1999 | Bantle |
| 6,627,400 B1 | 9/2003 | Singh et al. |

FOREIGN PATENT DOCUMENTS

| EP | 0 371 139 | 6/1990 |
| EP | 0 371 139 A | 6/1990 |
| EP | 0 748 800 | 12/1996 |
| EP | 0 748 800 A | 12/1996 |
| EP | 1 308 452 | 5/2003 |
| EP | 1 308 452 A | 5/2003 |
| JP | 62 174011 | 7/1987 |
| JP | 63 060929 | 3/1988 |
| JP | 63 165373 | 7/1988 |
| JP | 06065235 | 10/1995 |
| WO | WO 93/02044 | 2/1993 |
| WO | WO 93/02044 A | 2/1993 |
| WO | WO 95/18820 | 7/1995 |
| WO | WO 95/18820 A | 7/1995 |

OTHER PUBLICATIONS

Takaku et al., CAPLUS Abstract 109:211401 (1988).*
Takaku et al., CAPLUS Abstract 110:115272 (1989).*
Patent Abstract of Japan vol. 012, No. 283, Aug. 3, 1988.
Abstract. JP 63 0 60929 A. Mar. 17, 1988.
Patent Abstract of Japan. vol. 012, No. 022. Jan. 22, 1988.
Abstract. JP 62 174011 A. Jul. 30, 1987.
Patent Abstracts of Japan. vol. 012, No. 438, Nov. 17, 1988.
Abstract. JP 63 165373 A. Jul. 8, 1988.
Skaric, Vinko. et al., "Homologation and intramolecular cyclinzation reactions in aliphatic deoxyuridine analogs series," Croatica Chemica Acta, 56(1), 125-39. XP008047706. Abstract. (1983).
Bai-Chuan, Pan et al. "Synthesis A. Anti-HIV-1 activities of 6-arylthio . . . ," Journal of Heterocyclic Chemistry, Heterocorporation. Provo. US, vol. 31, No. 1, Jan. 1994. pp. 177-185. XP00220978.
US 2001/0020026, Jul. 2001, (withdrawn).
Skarik, et al., Croatica Chemica Acta, (1983), vol. 56 (1), pp. 125-139.
Bai-Chuan, et al., J Heterocyclic Chem, (1994), vol. 31 (1), pp. 177-185.
Takamatsu, et al., Nucleosides Nucleotides Nucleic Acids, (2002), vol. 21 (11&12), pp. 849-861.

(Continued)

*Primary Examiner*—Deepak Rao
(74) *Attorney, Agent, or Firm*—Birch, Stewart, Kolasch & Birch, LLP

(57) ABSTRACT

Deoxyuridine derivatives of the formula (I) where $R^1$ is H or various substituents; D is —NHCO—, —CONH—, -0-, —C(=O)—, —CH=CH, —C≡C—, —$NR^5$—; $R^4$ is hydrogen or various substituents; $R^5$ is H, $C_1$-$C_4$ alkyl, $C_1$-$C_4$ alkanoyl; E is Si or C; $R^6$, $R^7$ and $R^8$ are independently selected from $C_1$-$C_8$ alkyl, $C_2$-$C_8$ alkenyl, $C_2$-$C_8$ alkynyl or a stable monocyclic, bicyclic or tricyclic ring system; G is —O—, —S—, —$CHR^{10}$—, —C(=O)—; J is —$CH_2$—, or when G is $CHR^{10}$ may also be —O— or —NH—; $R^{10}$ is H, F, —$CH_3$, —$CH_2NH_2$, —$CH_2OH$; —$OHR^{11}$ is H, F, —$CH_3$, —$CH_2NH_2$, —$CH_2OH$, —CH(OH)$CH_3$, CH($NH_3$)$CH_3$; or $R^{10}$ and $R^{11}$ together define an olefinic bond, or together form a —$CH_2$-group, thereby defining a cis or trans cyclopropyl group; have utility in the prophylaxis or treatment of protozoal diseases such as malaria.

(I)

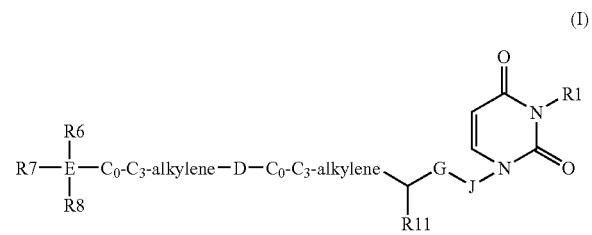

13 Claims, No Drawings

OTHER PUBLICATIONS

Von Janta Lipinski, et al. J Med Chem, (1998), vol. 41 (12), pp. 2040-2046.

Batoux, et al. Tetrahedron Lett, (2001), vol. 42 (8), pp. 1491-1493.

Sukeda, et al. J Org Chem, (2000), vol. 65 (26), pp. 8988-8996.

* cited by examiner

DUTPASE INHIBITORS

This application is a national phase under 35 U.S.C. §371 of PCT International Application No. PCT/GB2005/050002 which has an International filing date of Jan. 6, 2005, which designated the United States of America, and claims priority to Patent Application No. 0400290.3 filed in Great Britain, which has a filing date of Jan. 1, 2004, the entire contents of all applications listed above are hereby incorporated by reference.

FIELD OF THE INVENTION

The present invention relates to pharmaceuticals active against parasite dUTPase and methods for treating parasitical infections, especially malaria, by administering such compounds.

TECHNICAL BACKGROUND

Deoxyuridine triphosphate nucleotidohydrolase (dUTPase, E.C. 3.6.1.23) is an ubiquitous enzyme which hydrolyzes deoxyuridine triphosphate (dUTP) to deoxyuridine monophosphate (dUMP) and pyrophosphate, typically in the presence of magnesium ions. This reaction is thought to occur primarily to limit pools of intracellular dUTP in order to prevent significant uridine incorporation into DNA during replication and repair. A second role of dUTPase is to provide substrate (dUMP) for the de novo synthesis of thymidylate.

Two groups of researchers, McIntosh et al., PNAS, 89:8020-8024 (1992) and Strahler et al., PNAS, 90:4991-4995 (1993), have reportedly isolated the human dUTPase enzyme and characterized the enzyme by its cDNA and amino acid sequences.

McIntosh reported a cDNA of 526 base pairs containing an ORF which encoded a protein of 141 amino acids and a 3f flanking sequence following the ORF. Strahler reported the identical cDNA and amino acid sequence as did McIntosh, with the exception of two additional bases at the 51 end of the cDNA and a longer 3f flanking sequence. The human dUTPase reported by both groups was found to have a high degree of homology with dUTPase from other organisms including that from yeasts, bacteria and viruses. Strahler further reported that human dUTPase exists in both, phosphorylated and a non-phosphorylated forms.

International patent application no WO97/36916 discloses the sequence of nuclear and mitochondrial isoforms of dUTPase.

In both prokaryotic and eukaryotic cell systems, dUTPase has been clearly shown to be an essential enzyme, without which the cell will die. Lack of dUTPase leads to elevated cellular dUTP pools, resulting in an increased misincorporation of uridine into DNA. In addition to prokaryotes and eukaryotes, a number of viruses, such as herpes simplex, are known to encode a dUTPase function.

International patent application no WO95/15332 proposes a range of uridine di- and triphosphate analogues in which the oxygen atoms between phosphate groups are replaced with methylene, secondary amine or tertiary amine, and/or oxo functions on the phosphate are replaced with sulphur. These compounds are postulated as cytostatics for use against rapidly growing cancer cells and/or antivirals against herpes. Substantially similar compounds are disclosed in Zalud et al Adv. Exp. Med Biol. 1995 370 135-138 and Persson et al Bioorg Med Biochem 1996 4 553-556. It should be noted, however that these compounds have been primarily designed for crystallographic purposes and the analysis of enzyme kinetics. These compounds therefore do not possess physicochemical attributes suggestive of a drug.

The present inventors have established that the substrate specificity of the dUTPases of certain protozoal and bacterial parasites of man differ from the corresponding human cellular and mitochondrial enzymes to such an extent that a specific set of inhibitor compounds can be prepared which selectively inhibit the parasite dUTPase without substantially inhibiting the human counterparts. Examples of such parasites include *Plasmodium* species especially *P. falciparum* responsible for malaria, Mycobacterial species, especially *M tuberculosum* responsible for tuberculosis and *Leishmania* spp.

Hidalgo-Zarco and González-Pacanowska Current Protein and Peptide Science, 2001, 2, 389-397 describe the isolation and characterisation of trypanosomal dUTPases. In contrast to the trimeric form of dUTPase shared by human and malarial enzymes, the trypanosomal enzyme is a dimmer. Competitive inhibition of *Leishmania* dUTPase was shown by the triphosphate substrate analogue α-β-imido-dUTP, whereas no inhibition of that parasite was apparent in the case of 5'-O-(4-4'-dimethoxytrityl)-2'-deoxyuridine.

BRIEF DESCRIPTION OF THE INVENTION

A first aspect of the invention there provides the use of compounds of the formula I, in the manufacture of a medicament for the treatment or prophylaxis of parasitic infections in mammals, including man:

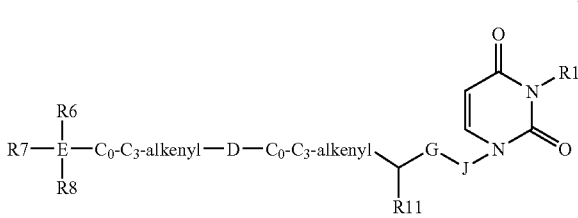

I wherein $R^1$ is H, $C_1$-$C_5$ alkyl, $C_2$-$C_5$ alkenyl, $C_2$-$C_5$ alkynyl or a 5 or 6 membered, saturated or unsaturated ring containing 0 to 3 heteroatoms selected from N, O and S, any of which is optionally substituted with $R^4$;

D is —NHCO—, —CONH—, —O—, —C(=O)—, —CH=CH—, —C≡C—, —$NR^5$—, $R^4$ is independently hydrogen, halo, cyano, amino, nitro, carboxy, carbamoyl, hydroxy, oxo, $C_1$-$C_5$ alkyl, $C_1$-$C_5$ haloalkyl, $C_1$-$C_5$ alkyloxy, $C_1$-$C_5$ alkanoyl, $C_1$-$C_5$ alkanoyloxy, $C_1$-$C_5$ alkylthio, —N($C_0$-$C_3$-alkyl)$_2$, hydroxymethyl, aminomethyl, carboxymethyl; —$SO_2$N($C_0$-$C_3$-alkyl), —$SO_2C_1$-$C_5$-alkyl;

$R^5$ is H, $C_1$-$C_3$ alkyl, $C_1$-$C_3$ alkanoyl;

E is Si or C;

$R^6$, $R^7$ and $R^8$ are independently selected from $C_1$-$C_8$ alkyl, $C_{2-8}$ alkenyl, $C_2$-$C_8$ alkynyl, or a stable monocyclic, bicyclic or tricyclic ring system which is saturated or unsaturated in which each ring has 0 to 3 heteroatoms selected from N, O and S, and wherein any of the $R^6$, $R^7$ and/or $R^8$ groups are optionally substituted with $R^4$;

G is —O—, —S—, —$CHR^{10}$—, —C(=O)—;

J is $CH_2$, or when G is $CHR^{10}$ may also be —O— or —NH—;

$R^{10}$ is H, $CH_3$, $CH_2NH_2$, $CH_2OH$, OH, or a pharmaceutically acceptable ether, amide or ester thereof;

$R^{11}$ is H, F, $CH_3$, $CH_2NH_2$, $CH_2OH$, $CH(OH)CH_3$, $CH(NH_2)CH_3$;

or a pharmaceutically acceptable ether, amide or ester thereof; or $R^{10}$ and $R^{11}$ together define an olefinic bond, or together form a —$CH_2$-group, thereby defining a cis or trans cyclopropyl group;

or a pharmaceutically acceptable salt thereof.

A second aspect of the Invention provides novel compounds of the formula II

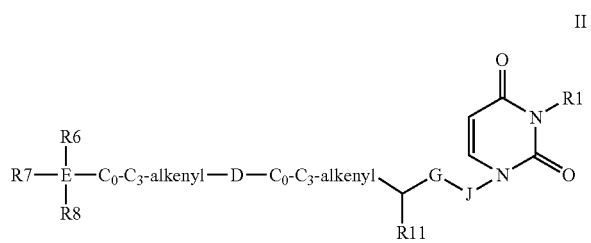

wherein $R^1$ is H, $C_1$-$C_5$ alkyl, $C_2$-$C_5$ alkenyl, $C_2$-$C_5$ alkynyl or a 5 or 6 membered, saturated or unsaturated ring containing 0 to 3 heteroatoms selected from N, O and S, any of which is optionally substituted with $R^4$;

D is —NHCO—, —CONH—, —O—, —C(=O)—, —CH=CH—, —C≡C—, —$NR^5$—, $R^4$ is hydrogen, halo, cyano, amino, nitro, carboxy, carbamoyl, hydroxy, oxo, $C_1$-$C_5$ alkyl, $C_1$-$C_5$ haloalkyl, $C_1$-$C_5$ alkyloxy, $C_1$-$C_5$ alkanoyl, $C_1$-$C_5$ alkanoyloxy, $C_1$-$C_5$ alkylthio, —$N(C_0$-$C_3$-alkyl$)_2$, hydroxymethyl, aminomethyl, carboxymethyl; —$SO_2N(C_0$-$C_3$-alkyl), —$SO_2C_1$-$C_5$-alkyl;

$R^5$ is H, $C_1$-$C_3$-alkyl, $C_1$-$C_3$-alkanoyl;

E is Si or C;

$R^6$ and $R^7$ are independently selected from a stable monocyclic, bicyclic or tricyclic ring system which has an aromatic nature wherein each ring has 0 to 3 heteroatoms selected from N, O and S;

$R^8$ is selected from $C_1$-$C_8$ alkyl, $C_2$-$C_8$ alkenyl, $C_2$-$C_8$ alkynyl, or a stable monocyclic, bicyclic or tricyclic ring system which is saturated or unsaturated and in which each ring has 0 to 3 heteroatoms selected from N, O and S; wherein
$R^6$, $R^7$ and $R^8$ groups are independently optionally substituted with $R^4$;

G is —O—, —S—, —$CHR^{10}$—, —C(=O)—;

J is $CH_2$, or when G is $CHR^{10}$ may also be —O— or —NH—;

$R^{10}$ is H, $CH_3$, $CH_2NH_2$, $CH_2OH$, OH; or a pharmaceutically acceptable ether, amide or ester thereof;

$R^{11}$ is H, F, $CH_3$, $CH_2NH_2$, $CH_2OH$, $CH(OH)CH_3$, $CH(NH_2)CH_3$; or a pharmaceutically acceptable ether, amide or ester thereof; or $R^{10}$ and $R^{11}$ together define an olefinic bond, or together form a —$CH_2$-group, thereby defining a cis or trans cyclopropyl group;

or a pharmaceutically acceptable salt thereof.

The potency and selectivity of the compounds and methods of the invention, which presuppose substantial lipophilicity at the 5' position is surprising bearing in mind that the active site of the dUTPase enzyme is intended to recognize and accommodate highly polar, hydrophilic moieties, ie the triphosphorylated nucleotides.

Preferably G is —O—, that is an N-1 methyloxymethyluridine derivative or —$CH_2$—, that is an N-1-alkyl derivative. Additional preferred variants at this position include wherein G is —$CH(CH_2OH)$— or wherein $R^{10}$ and $R^{11}$ define an olefinic bond or a cyclopropyl group.

Preferred $R^{11}$ groups include H and $CH_2OH$ or lipophilic ethers or esters thereof such as a straight or branched chain alkyl or benzyl ester or an ether such as straight or branched chain alkyl or benzyl ether or an alkylated silyl function. Other preferred $R^{11}$ group include $CH_2NH_2$ and pharmaceutically acceptable amides thereof.

Certain preferences of the invention tend to be applicable to both formula I and II. For example $R^1$ is preferably a small substituent, most preferably H.

Favoured $C_0$-$C_3$-alkylene-D-$C_0$-$C_3$-alkylene- configurations include aminomethylene, aminoethylene and aminopropylene, methylaminomethylene, methylaminoethylene, ethylaminomethylene, —(N-methyl)aminomethylene, —(N-methyl)aminoethylene, —(N-methyl)aminopropylene and methyl-(N-methyl)aminomethylene. Currently the most preferred is -aminomethylene-. The order of the hetero atom D and alkylene moieties in the indicated groups as used herein corresponds to the configuration of Figure I or II as depicted above, that is "aminomethylene" has the nitrogen atom adjacent E and the methylene moiety proximal to the base.

Particularly preferred $C_0$-$C_3$-alkylene-D-$C_0$-$C_3$-alkylene- configurations include —O—, oxymethylene, oxyethylene, oxypropylene methyloxymethylene and methyloxyethylene. Currently the most preferred in this series is -oxymethylene-.

Preferably at least one of $R^6$, $R^7$ and/or $R^8$ has an aromatic nature, although this tends to be less important if $R^{11}$ has a lipophilic nature. Conveniently two of $R^6$, $R^7$ and/or $R^8$ have an aromatic nature and the invention even embraces compounds wherein all three have an aromatic nature.

Ring systems for $R^6$, $R^7$ and/or $R^8$ are typically bonded direct to E, but may optionally be bonded to E via a methylene linker. For example $R^6$ may be optionally substituted benzyl, thereby representing phenyl bonded through a methylene to E.

Ring systems having an aromatic nature for $R^6$, $R^7$ and/or $R^8$ include phenyl and heteroaryls such as furyl, thienyl, pyrrolyl, pyrazolyl, imidazolyl, pyridyl, pyrimidinyl, pyridazinyl, oxazolyl, isoxazolyl, thiazolyl, isothiazolyl, especially pyridyl. Ring systems having an aromatic nature also include multi-ring systems wherein only one ring has an aromatic nature such as indolinyl and ring systems wherein more than one ring has an aromatic nature such as naphthyl, or any of the above heteroarylic rings fused to phenyl, such as benzimidazolyl.

Convenient values for $R^6$, $R^7$ and/or $R^8$ include optionally substituted heterocycles such as furyl, thienyl, pyranyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, especially pyridyl, and optionally substituted carbocycles such as cycloalkyl, cycloalkenyl and especially phenyl. Alternative values for $R^6$, $R^7$ (use aspects only) and/or $R^8$ include straight or branched alkyl, including methyl, ethyl, i-propyl and t-butyl.

Favoured $(R^6)(R^7)(R^8)$-E- configurations include —C(Ph)$_3$, —CH(Ph)$_2$, —CH$_2$Ph, —Si(Ph)$_2$(t-Bu), 1,1-bis (4-methylphenyl)-1'-pyrenylmethyl, where Ph is phenyl or phenyl substituted with $R^4$.

The optional substituent to $R^6$, $R^7$, and/or $R^8$ include 1 to 3, preferably 1 substituent per ring, selected from halo, preferably fluoro, cyano (preferably cyano), amino, nitro, carboxy, carbamoyl, hydroxy, oxo, $C_1$-$C_5$ alkyl, preferably methyl or t-butyl, $C_1$-$C_5$ haloalkyl, preferably trifluoromethyl, $C_1$-$C_5$ alkyloxy, preferably methoxy, $C_1$-$C_5$ alkanoyl, preferably acetyl, $C_1$-$C_5$ alkanoyloxy, preferably acetoxy, $C_1$-$C_5$ alkylthio, —N(C$_0$-C$_3$-alkyl)$_2$, preferably NHMe or NMe, hydroxymethyl, aminomethyl, carboxymethyl; —SO$_2$N(C$_0$-C$_3$-alkyl), preferably SO$_2$NH$_2$ or SO$_2$NMe$_2$ or —SO$_n$C$_1$-C$_5$-alkyl, preferably sulphonylmethyl or sulphinylmethyl.

Although the applicant is not currently aware of any such compounds, it may be desirable for novelty reasons to exclude (in the present compound claims only) certain compounds with common protecting groups at the (nominal) 5'-oxygen of the acyclic nucleoside, for example 5'-O-trityl, methoxylated 5'-O-trityl or 5'-O-tert.butyldiphenylsilyl, or maybe other individual hydroxyl protecting groups as discussed by Greene below. Intuitively, such a proviso is more likely to be the case in acyclic nucleosides closely resembling native nucleosides, ie where $C_0$-$C_3$-alkyl-D-$C_0$-$C_3$ alkyl is —O—CH$_2$—, especially when G is O, J is CH$_2$ and $R^{11}$ is H or —CH$_2$OH. Any such future avoidance of, say, trityl or tBuPh$_2$Si (in the compound claims only) is less likely to be required in respect of other permutations of $C_0$-$C_3$-alkyl-D-$C_0$-$C_3$ alkyl, such as compounds wherein D is N. The novel compounds of the invention will however typically avoid hydroxyl protecting groups, such as those cited in Greene below, when $C_0$-$C_3$ alkyl-D-$C_0$-$C_3$ alkyl is —O—CH$_2$—. Compounds bearing such common protecting groups will still be amenable to the use/method aspects of the invention as illustrated in the accompanying examples.

Compounds wherein E is carbon are currently favoured on pharmaco-kinetic grounds, although compounds with E as Si have shown advantageous potency and selectivity.

The compounds of the Invention include a number of chiral centres, and the invention extends to include racemates, enantiomers and stereoisomers at each of these centres.

Similarly, the invention extends to all stereochemistries around G (as CHR$^{10}$, where $R^{10}$ is other than H) and $R^{11}$ in Figure I and II, including cis and trans cyclopropyl for $R^{10}$ and $R^{11}$ Compounds of the Invention are generally at least 80% preferably at least 90% such as 97% stereoisometrically pure at chiral centres.

In some embodiments, it is preferred that if $R^{11}$ is H, CH$_3$, CH$_2$NH$_2$ CH$_2$OH, a bond or —CH$_2$—, then at least one of $R^6$, $R^7$ and/or $R^8$ comprises an unsaturated ring.

Additional aspects of the invention include a pharmaceutical composition comprising a compound of the formula II in conjunction with a pharmaceutically acceptable carrier or diluent therefor. The invention further provides a method for the treatment or prophylaxis of parasite infections, such as malaria, in man or a zoonose vector comprising the administration of an effective amount of a compound of formula I to a patient in need thereof, or to the vector. Alternative parasitic infections include human African trypanosomiasis or Chagas disease.

While it is possible for the active agent to be administered alone, it is preferable to present it as part of a pharmaceutical formulation. Such a formulation will comprise the above defined active agent together with one or more acceptable carriers or excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula I or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethyl cellulose, sucrose and starch; fillers and carriers, for example corn starch, gelatine, lactose, sucrose, microcrystalline cellulose, kaolin, mannitol, dicalcium phosphate, sodium chloride and alginic acid; and lubricants such as magnesium stearate, sodium stearate and other metallic stearates, stearic acid, glycerol stearate, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier. Dosages are set in the conventional manner to take into account the severity of the disease, the susceptibility of the parasite strain, the size and metabolic health of the patient, the mode and form of administration, concomitant medication and other relevant factors. The compounds of the invention may be administered at a daily dose generally in the range 0.1 to 200 mg/kg/day, advantageously, 0.5 to 100 mg/kg/day, more preferably 10 to 50 mg/kg/day, such as 10 to 25 mg/kg/day. A typical dosage rate for a normal adult will be around 50 to 500 mg, for example 300 mg, once or twice per day.

The compounds of formula I and formula II can form salts which form an additional aspect of the invention. Appropriate pharmaceutically acceptable salts of the compounds of formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Examples of monocyclic rings for $R^1$ include heterocycles such as furyl, thienyl, pyranyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, especially pyridyl, and carbocycles such as $C_3$-$C_7$ cycloalkyl, especially cyclopentyl or cyclohexyl, $C_5$-$C_7$ cycloalkenyl and phenyl.

Examples of monocyclic, bicyclic or tricyclic rings for $R^6$, $R^7$ and/or $R^8$ include heterocycles such as furyl, thienyl, pyranyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, thiadiazolyl, tetrazolyl, triazolyl, and the like or bicyclic rings especially of the above fused to a phenyl ring such as indolyl, quinolyl quinolinyl, isoquinolinyl, benzimidazolyl, benzothiazolyl, benzoxazolyl, benzotriazolyl, benzofuryl, benzothienyl etc. Additional rings include xanthenyl (such as 9-xanthenyl, 9-alkylxanthenyl, 9-(9-alkyl)xanthenyl, 9-phenylxanthenyl, 9-(9-phenyl)xanthenyl, 9-heteroarylxanthenyl, 9-(9-heteroaryl)xanthenyl), dibenzosuberyl, 5-dibenzosuberyl, fluorenyl (such as 5-fluorenyl, 5-(5-alkyl)fluorenyl, 5-(5-phenyl)fluorenyl, 5-(5-heteroaryl)fluorenyl) and the like.

Examples of monocyclic, bicyclic or tricyclic ring systems with an aromatic nature for $R^6$ and/or $R^7$ include heteroaryls such as furyl, thienyl, pyrrolyl, pyrazolyl, imidazolyl, pyridyl, pyrazinyl, pyrimidinyl, pyridazinyl, oxazolyl, isoxazolyl, thiazolyl, isothiazolyl, thiadiazolyl, tetrazolyl, triazolyl, and the like or bicyclic rings especially of the above fused to a phenyl ring such as indolyl, quinolyl quinolinyl, isoquinolinyl, benzimidazolyl, benzothiazolyl, benzoxazolyl, benzotriazolyl, benzofuryl, benzothienyl etc. Additional rings include xanthenyl (such as 9-xanthenyl, 9-alkylxanthenyl, 9-(9-alkyl)xanthenyl, 9-phenylxanthenyl, 9-(9-phenyl)xanthenyl, 9-heteroarylxanthenyl, 9-(9-heteroaryl) xanthenyl), dibenzosuberyl, 5-dibenzosuberyl, fluorenyl (such as 5-fluorenyl, 5-(5-alkyl)fluorenyl, 5-(5-phenyl)fluorenyl, 5-(5-heteroaryl)fluorenyl) and the like.

Examples of carbocycles for $R^6$, $R^7$ and/or $R^8$ include monocyclic rings such as phenyl, cyclohexenyl, cyclopentenyl, cyclohexanyl, cyclopentanyl, bicyclic rings such as indanyl, napthyl, and tricyclic rings such as adamantyl, and the like.

The carbo or heterocyclic ring may be bonded via a carbon or via a hetero atom, typically a nitrogen atom, such as N-piperidyl, N-morpholinyl etc. Other examples of such ring systems may also be found in J. Fletcher, O. Dermer, R. Fox, Nomenclature of Organic Compounds, pp. 2063 (1974).

The term "$C_1$-$C_5$ alkyl" includes such groups as methyl, ethyl, n-propyl, isopropyl, n-butyl, s-butyl, t-butyl, cyclopropyl, n-pentyl and the like with $C_1$-$C_8$ alkyl further including n-hexyl, 3-methylpentyl, and the like.

The term "halo" and "halogen" refer to chloro, bromo, iodo, and especially fluoro.

"$C_1$-$C_5$ alkoxy" refers to those groups such as methoxy, ethoxy, propoxy, t-butoxy and the like.

"$C_2$-$C_6$ alkenyl" refers to those groups such as vinyl, 1-propen-2-yl, 1-butene-4-yl, 1-pentene-5-yl, 1-butene-1-yl and the like, with $C_2$-$C_8$ alkenyl further including hex-3-enyl and the like.

"$C_1$-$C_5$ alkylthio" refers to those groups such as methylthio, ethylthio, t-butylthio, and the like.

"$C_1$-$C_5$ alkanoyl" refers to groups such as acetyl, propionyl, butyryl and the like.

"$C_1$-$C_5$ alkanoyloxy" refers to those groups such as acetoxy, propionoxy, formyloxy, butyryloxy, and the like.

The term "$C_2$-$C_8$ alkenoxy" includes groups such as ethenyloxy, propenyloxy, iso-butoxy ethenyl, and the like.

The term "$C_2$-$C_5$ alkynyl" includes groups such as ethynyl, propynyl, butynyl, pentynyl, and the like with $C_2$-$C_8$ alkynyl further including hexynyl and the like.

The term "halo $C_1$-$C_5$ alkyl" includes alkyls substituted 1, 2 or 3 times by a halogen including groups such as trifluoromethyl, fluoromethyl, 2-dichloroethyl, 2,2-difluoroethyl, 2,2,2-trifluoroethyl, 3,3-difluoropropyl, 1,1-2,2,2 pentafluoroethyl and the like.

The term —$C_0$-$C_3$-alkylene- as a bivalent in expressions such as —$C_0$-$C_3$-alkylene-D-$C_0$-$C_3$-alkyl includes a bond (i.e $C_0$), methylene ($C_1$), ethylene ($C_2$), 1,1-dimethyl-methylene ($C_3$), propylene ($C_3$) and the like, with each —$C_0$-$C_3$-alkylene- being selected independently.

The term ($C_0$-$C_3$-alkyl) in monovalent expressions includes H (i.e $C_0$), Me ($C_1$), Et ($C_2$), propyl ($C_3$) with each $C_0$-$C_3$-alkyl being selected independently. Accordingly —N($C_0$-$C_3$-alkyl)$_2$ includes —$NH_2$, —NHMe, NHEt NHPr, —N(Me)$_2$, N(Et)$_2$ etc, —$SO_2$N($C_0$-$C_3$-alkyl)$_2$, includes —$SO_2NH2$, —$SO_2$NHMe, —$SO_2$N(Me)$_2$ etc As used herein, "the esters, amides and ethers thereof" refer to the appropriate derivatives of each of the preceding hydroxyl and/or amino groups in the immediately preceding definition. For example the ethers and esters of $R^{10}$ or $R^{11}$ include those of the indicated $CH_2OH$, $CH(OH)CH_3$ groups by esterification or alkylation, and the amides include those formed by reaction of an amine with either of these groups or by reaction of a carboxylic acid with the indicated —$CH_2NH_2$ or $CH(NH_2)CH_3$ moieties.

Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); amino acid esters (for example, L-valyl or L-isoleucyl); and mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises an optionally $R^4$-substituted phenyl group.

Pharmaceutically acceptable esters include $C_1$-$C_{22}$ fatty acid esters, such as acetyl, t-butyl or long chain straight or branched unsaturated or omega-6 monounsaturated fatty acids such as palmoyl, stearoyl and the like.

Alternative aryl or heteroaryl esters include benzoyl, pyridylmethyloyl and the like any of which may be substituted with $R^4$, Preferred pharmaceutically acceptable esters include aliphatic L-amino acid esters such as leucyl, isoleucyl and especially valyl. Additional preferred amino acid esters include the 2-O-AA-$C_3$-$C_{22}$ fatty acid esters described in WO99 09031, where AA is an aliphatic amino acid ester, especially those derived from L-lactic acid and L-valyl.

Pharmaceutically acceptable ethers include straight or branched chain saturated or omega 6 unsaturated $C_1$-$C_{22}$ alkyl ethers such as methyl ethers, t-butyl ethers or aryl or heteroaryl ethers such as phenoxy, benzylether, pyridylmethyl ether, any of which may be substituted with $R^4$.

Alternative ethers include alkylated silyl functions such as —Si($C_1$-$C_5$-alkyl)$_3$ such as —Si(t-Bu)(CH$_3$)$_2$, or —Si(Ph)$_2$(t-Bu), —C(Ph)$_3$ (trityl), —CH(Ph)$_2$, —CH$_2$Ph, 1,1-bis(4-methylphenyl)-1'-pyrenylmethyl and the like.

Pharmaceutically acceptable amides include those derived from $C_1$-$C_{22}$ branched or straight chain carboxylic acid, optionally including 1 to 3 unsaturations, or anilines or benzylamines. Preferred amides include those formed from $C_1$-$C_4$ straight or branched chain alkanoic acids, such as acetyl. Other pharmaceutically acceptable amides of amine functions of $R^{10}$ or $R^{11}$ correspond to the preferred esters indicated above.

It is currently preferred that the ester, amide or ether is lipophilic in nature.

Compounds of the invention are typically synthesized as outlined below.

A useful intermediate for the preparation of compounds according to the invention can be synthesized as illustrated in scheme 1.

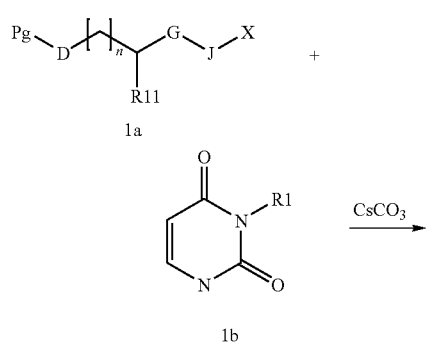

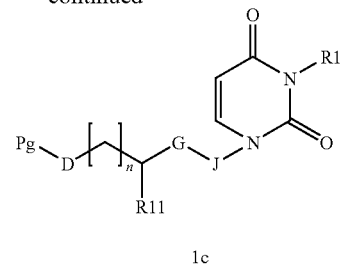

n is 0, 1, 2, 3

An alkyl chain can be coupled to a uracil derivative (1b) by a displacement reaction with a suitably protected alkylating agent (1a) to give the acyclic nucleoside analogue (1c). $R^1$, G, J and $R^{11}$ are as defined for formula I and II, D is NH or O, Pg is a suitable protecting group and X is a halide like chloride or bromide.

The provided intermediate compound can then be further reacted as shown in scheme 2 to obtain compounds of general formula I and II.

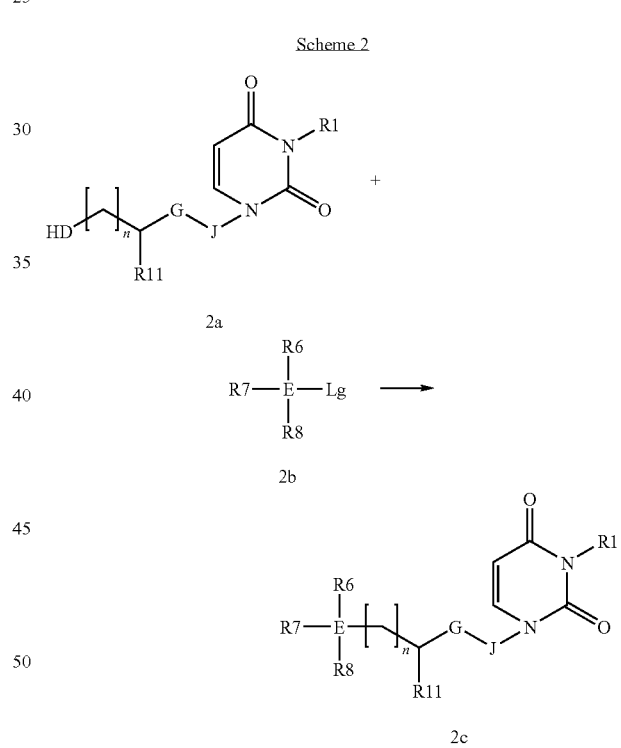

n is 0, 1, 2, 3

Removal of the protecting group from compound 1c using conventional methods followed by reaction of the amine or alcohol (2a) with an alkylating agent of formula 2b wherein $R^6$, $R^7$, $R^8$ and E are as defined above for formula I and Lg is a leaving group, in a solvent like pyridine optionally in the presence of a catalyst such as dimethylaminopyridine or in a solvent like dimethylformamide in the presence of a catalyst like imidazole, provides the alkylated acyclic nucleoside analogue (2c). Various alkylating agents (2b) are available either commercially or in the literature, see for example Greene, "Protective Groups in Organic Synthesis (John Wiley & Sons, New York, 1981). For example, they can be prepared by transforming the hydroxy group of the corresponding alcohol into a leaving group such as a halide like chloride or bromide by treatment with a halogenating agent such as acetyl bromide or thionyl chloride or the like or they can be transformed into a derivative of sulfonic acid like a mesyl, tosyl, triflate or the like by treatment with for example the anhydride or acid chloride of the desired sulfonic acid derivative. Alkylating agents (2b) can also be prepared as shown in scheme 3.

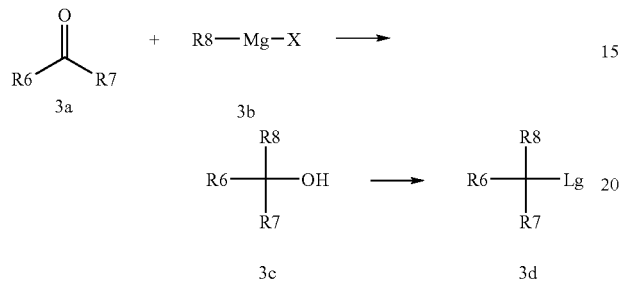

Reaction of an electrophilic carbonyl compound like a keto compound (3a) or any carboxylic acid derivative for instance an ester or acid halide, and a suitable nucleophile for example a Grignard reagent (3b) or an organolithium reagent, provides a tertiary alcohol (3c). The formed hydroxy group can subsequently be transformed into a leaving group as described above. Examples of the above procedure are described in the literature, see for example Hodges et al., J. Org. Chem. 56, 1991, 449-452, and Jones et al., J. Med. Chem. 33, 1990, 416-419.

Compounds wherein the leaving group in compound 2b is spaced from the atom E by a $C_1$-$C_3$-alkylene chain, available either commercially or in the literature, may also be used as alkylating agents in scheme 1. An example of a route to a compound containing a $C_2$-alkylene chain is shown in scheme 4.

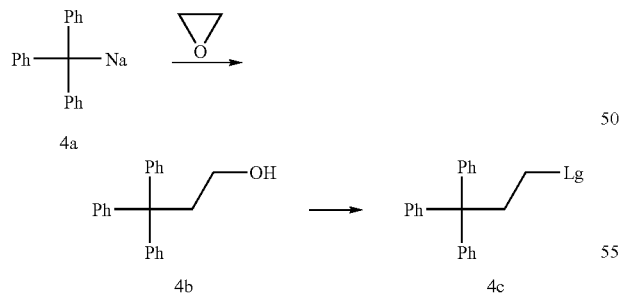

A reaction performed with triphenylmethyl sodium (4a) and ethylene oxide provides alcohol (4b). Subsequent transformation of the hydroxy group into a leaving group for example as described above provides alkylating agent (4c). Use of any other appropriate electrophilic reagent for example formaldehyde, provides analogues with other length of the $C_1$-$C_3$-alkyl chain. Se for example Wooster et al., J. Amer. Chem. Soc., 60, 1938, 1666 and McPhee et al., J. Amer. Chem. Soc. 65, 1943, 2177, 2180. Alternatively, alkylating agents containing a $C_1$-$C_3$-alkyl chain may be obtained by reduction of an appropriate acyl derivative to the desired alcohol.

An alternative route to acyclic and carba acyclic nucleoside analogues is shown in scheme 5.

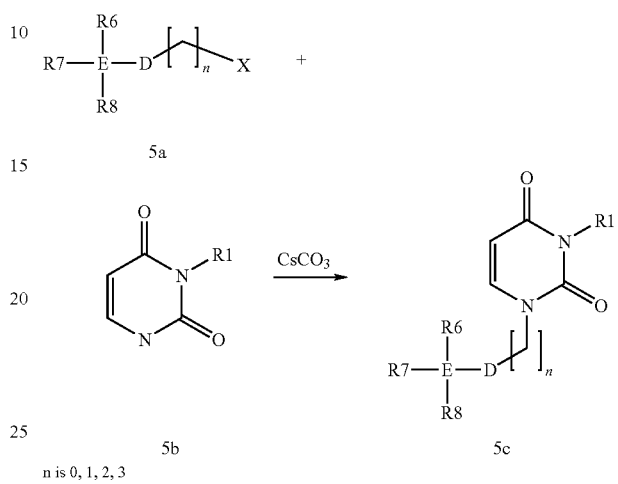

n is 0, 1, 2, 3

Alkylation of optionally N-substituted uracil (5b) with an alkylating agent (5a) wherein $R^6$, $R^7$, $R^8$ and E are as defined above, D is O or NH and X is a leaving group such as chloride or bromide, in the presence of a base such as cesium carbonate in a solvent like dimethylformamide, provides 5c.

The uracil substituent can also be introduced by way of a Mitsunobu reaction as shown in scheme 6.

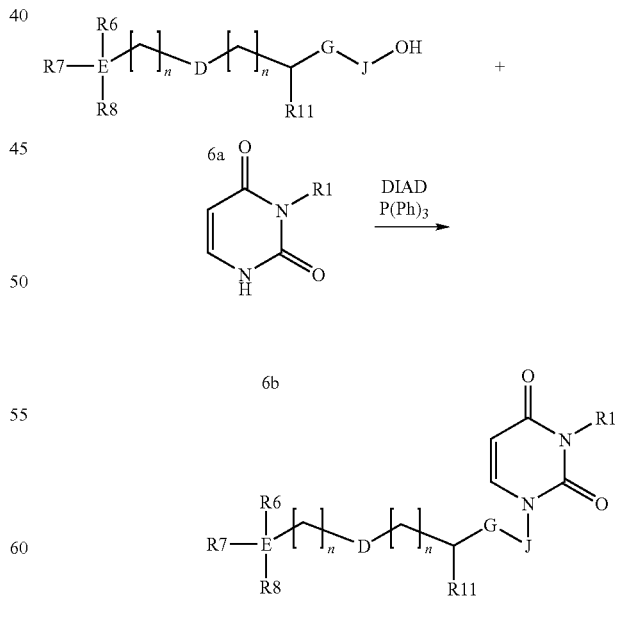

n is 0, 1, 2, 3

Treatment of alcohol (6a) and uracil derivative (6b) with triphenyl phosphine and DIAD in a solvent like THF provides the alkylated uracil derivative (6c).

Various acyclic side chains may be prepared as depicted in scheme 7.

Scheme 7

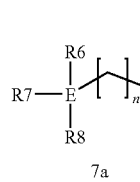

7a

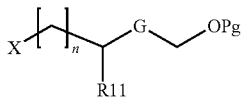

7b

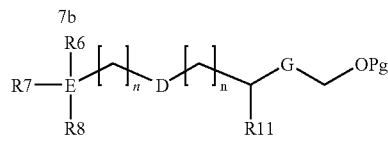

7c n is 0, 1, 2, 3

Reaction of a nucleophilic compound (7a) where $R^6$, $R^7$, $R^8$ and E are as defined above and D is O or NH, in a displacement reaction with an alkylating agent (7b) where $R^{11}$ and G are as defined above and X is a leaving group such as a halide like chloride or bromide and Pg is a hydroxy protecting group, in a solvent like dimethylformamide in the presence of an appropriate base such as sodium hydride or a carbonate provides acyclic side chains (7c). Removal of the hydroxy protecting group from the afforded side chain (7c) using conventional methods, provides compounds that can be coupled to the desired uracil derivative according to the method described in scheme 6. Alternatively, the hydroxy group can be transformed into a leaving group and coupled to the uracil derivative as described in scheme 5.

Acyclic nucleoside analogues used for the preparation of compounds according to the present invention are available either commercially or in the literature or they can be prepared as described herein. For example 1-(2'-hydroxyethoxymethyl)-uracil and 1-(2'-aminoethoxymethyl)-uracil are described by Kelley et al. in J. Med. Chem, 1981, 472-475 and J. Med. Chem, 1981, 753-756 respectively, the unsaturated compound 1-(hydroxy-2'-butenyl)uracil can be prepared in analogy with the corresponding thymine derivative as described by Zemlicka et al. in J. Med. Chem., 34, 1991, 421-429. Cyclopropyl carbocyclic nucleosides are described for example by Chu et al. in J. Org. Chem., 60, 1995, 5236 and Tet. Letters, 37, 1996, 8849-8851. Acyclic uridine analogues useful for the preparation of compounds according to the general formula (II) wherein J is O are described for instance by Harnden et al. in J. Chem. Soc. Perkin Trans., 1990, 2175-2183. Compounds wherein J is N can be prepared by condensation of 1-aminouracil with an appropriate aldehyde, as described for 9-aminoalkylguanines by Hamden et al. in Tet. Letters, 29, 1988, 5995-5998.

DETAILED DESCRIPTION OF THE EMBODIMENTS

Various aspects of the Invention will now be described by way of illustration only with reference to the following non-limiting examples, showing compounds of the invention and intermediates therefor. Note that the exemplified intermediates, such as the acyclic side chain building blocks are readily reacted with alternative bases to form additional compounds of the invention.

Example 1

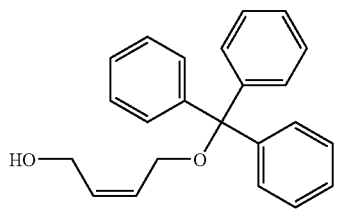

4-Trityloxy-but-2-en-1-ol (1)

Trityl chloride (557 mg; 2 mmol) Et$_3$N (0.306 ml; 2.2 mmol) and DMAP (10 mg; 0.08 mmol) were added to an emulsion of cis-2-buten-1,4-diol (1.76 g; 20 mmol) in DCM (10 ml). The mixture was stirred at room temperature under atmosphere of nitrogen for 24 hours. After such period of time the complete disappearance of trityl chloride was observed by TLC (EtOAC/Hexane 50:50). DCM (20 ml) and water (10 ml) were added to the mixture. The phases were separated and the organic layer was washed with water (10 ml) and brine (10 ml). The solvent was dried over MgSO$_4$ and evaporated under reduced pressure affording a residue (white oil) which was purified by flash chromatography using Hexane/EtOAc 70:30→40:60 as gradient which gave the title product as a colourless oil (563 mg, 81%).

Example 2

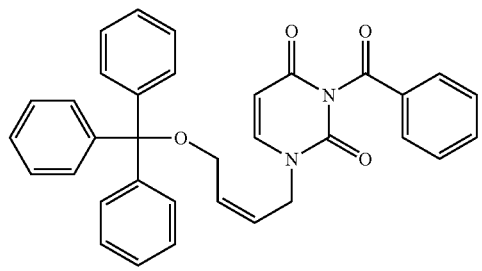

3-benzoyl-1-[(Z)-4-(trityloxy)-2-butenyl]-1,2,3,4-tetrahydro-2,4-pyrimidinedione (2)

Polymer bound triphenylphosphine (0.75 g; 2.25 mmol) was shaken in THF (5 ml) for 15 minutes, then 3-benzoyluracil (290 mg, 1.35 mmol) and tritylated alcohol (1) (300 mg; 0.90 mmol) were added to the suspension of the resin. A solution of DIAD (0.354 ml; 1.80 mmol) in THF (2 ml) was added to the mixture. The reaction was shaken 24 hours at room temperature and monitored by TLC (Hexane/EtOAc 50:50). The resin was filtered and washed twice with THF (5 ml). The filtrate was concentrated under reduced pressure and taken in EtOAc (5 ml), a white solid precipitated. The precipitate was filtered, the filtrate was concentrated again and purified by flash chromatography using Hexane/EtOAc as eluent which gave the title compound as a colourless oil (136 mg, 29%).

Example 3

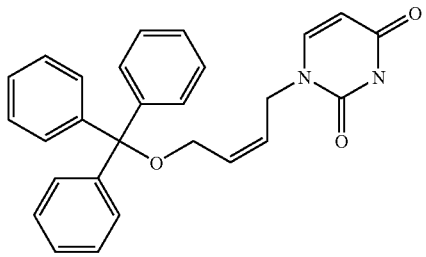

1-(4-Trityloxy-but-2-enyl)-1H-pyrimidine-2,4-dione (3)

A suspension of compound (2) (50 mg; 0.095 mmol) in MeONa/MeOH 0.2 M (5 ml) was stirred at room temperature for 24 hours. During such period of time the suspension became a colourless solution and the TLC (DCM/MeOH 90:10) showed the complete disappearance of the starting amide, and the presence of a new spot at lower $R_f$. The solution was neutralised with Dowex ion exchange resin. The resin was filtered off and washed twice with MeOH (5 ml). The filtrate was concentrated under reduced pressure and purified by flash chromatography using MeOH/DCM 10:90 as eluent which gave the title compound as a white solid (38 mg, 90%). $R_f$: 0.66 in DCM/MeOH 90:10.

$^1$H-NMR (300 MHz, CDCl$_3$): δ 8.21 (bs; 1H; NH); 7.52-7.49 (m; 6H; H-meta); 7.41-7.29 (m; 9H; H-orto+H-para); 7.16 (d; J=7.95 Hz; 1H; H-6); 6.09-6.01 (m; 1H; H-8); 5.69-5.98 (m; 2H; H-5+H-9); 4.28 (d; J=7.40 Hz; 2H; H-10); 3.79 (d; J=6.20 Hz; 2H; H-7).

$^{13}$C-NMR (75 MHz, CDCl$_3$): δ 164.0 (C-4); 1512 (C-2); 144.2 (C-6); 144.1 (C-12); 132.5 (C-8); 129.0 (C-13); 128.4 (C-14); 127.7 (C-15); 126.1 (C-9); 102.1 (C-5); 87.8 (C-11); 59.9 (C-10); 44.9 (C-7).

LRMS (ES+): m/z 447.2 [M+Na]$^+$ 100%.

HRMS (ES+): found 447.1680; required 447.1679 [M+Na]$^+$.

Example 4

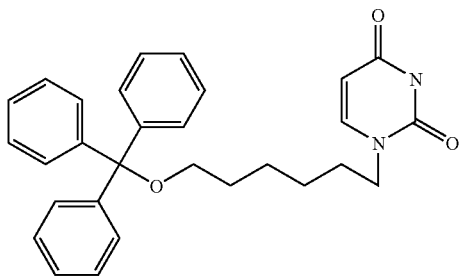

1-[3-(Triphenyl-methanoxy)-propyl]-1H-pyrimidine-2,4-dione or 1-(3'-trityloxylpropyl)uracil (4)

A mixture of 3-bromo-1-O-trityl propanol (400 mg, 1.05 mmol), cesium carbonate (385 mg, 1.05 mmol) and uracil (129 mg, 1.15 mmol) in DMF (10 ml) was warmed to 40° C. under atmosphere of nitrogen. After 4 hours the TLC showed the disappearance of the starting material, then water (10 ml) was added into the suspension, and extracted with EtOAc (3×15 ml). The organic layer was washed with brine, dried and the solvent was removed under reduced pressure to give a crude residue purified by flash chromatography to afford the desired compound as a white solid (134 mg, 31%).

$^1$H-NMR (300 MHz; CDCl$_3$) δ 2.08 (2H, m, 2'-H), 3.22 (2H, t, J=5.67 Hz, 1'-H), 4.02 (2H, t, J=6.58 Hz, 3'-H), 5.47 (1H, dd, J=2.37, 7.87 Hz, 5-H), 6.95 (1H, d, J=7.87 Hz, 6-H), 7.22-7.50 (15H, m, Ph-H), 8.10 (1H, bs, 3-NH).

Example 5

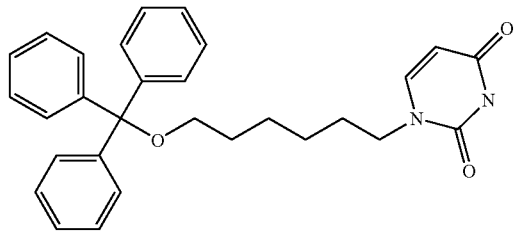

1-(4'-trityloxyhexyl)uracil (5)

A solution of uracil (0.066 g, 0.59 mmol) and caesium carbonate (0.135 g, 0.41 mmol) in dry DMF (4 mL) was stirred at room temperature under nitrogen for 10 min. 6-Bromo-1-O-tritylhexanol (0.170 g, 0.40 mmol) in dry DMF (1 mL) was added drop-wise via a syringe. The reaction mixture was stirred at 50° C. for 24 h and then left to cool down. Water (10 mL) was added and the solution was extracted with EtOAc (3×10 mL). The organic extracts were pooled, washed with brine (10 mL), dried over MgSO$_4$ and concentrated in vacuo, yielding a transparent liquid. This crude material was chromatographed on a silica gel column (Isolute SI column) using a gradient elution of 0→2% CH$_3$OH in CHCl$_3$. The title compound was obtained as a white solid (115 mg, 63%).

$^1$H NMR (300 MHz, CDCl$_3$) δ1.28-1.52 (4H, m, 3'-H and 4'-H), 1.69 (4H, m, 2'-H and 5'-H), 3.11 (2H, t, J=6.4 Hz, 6'-H), 3.72 (2H, t, J=7.3 Hz, 1'-H), 5.73 (1H, d, J=7.8 Hz, 5-H), 7.12 (1H, d, J=7.7 Hz, 6-H), 7.23-7.40 (9H, m, Ph-H), 7.50 (6H, m, Ph-H), 9.98 (1H, bs, 3-NH).

$^{13}$C NMR (75 MHz, CDCl$_3$) δ 26.3 (3'-CH$_2$ or 4'-CH$_2$), 26.7 (3'-CH$_2$ or 4'-CH$_2$), 29.4 (2'-CH$_2$ or 5'-CH$_2$), 30.3 (2'-CH$_2$ or 5'-CH$_2$), 49.3 (1'-CH$_2$ or 6'-CH$_2$), 63.7 (1'-CH$_2$ or 6'-CH$_2$), 86.8 (1"-C), 102.5 (5-CH), 127.3 (Ph-CH), 128.2 (Ph-CH), 129.1 (Ph-CH), 144.8 (Ph-C), 144.9 (6-CH), 151.5 (2-C), 164.7 (4-C).

ES$^+$ m/z (%) 477 ([M+Na]$^+$, 100), 243 (Ph$_3$C$^+$, 58).

HRMS (ES$^+$) Found [M+NH$_4$]$^+$ 472.2592; C$_{29}$H$_{34}$N$_3$O$_3$ requires 472.2595.

IR (KBr) 3052, 2940, 1712 (weak), 198, 1666, 1468, 1426, 1359, 758, 704 cm$^{-1}$.

M.p. 155-156° C.

Example 6

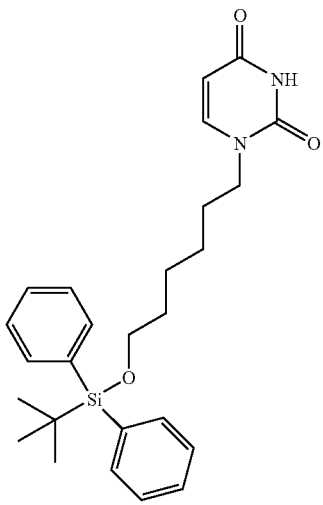

1-(4'-tert-butyldiphenylsilyloxyhexyl)uracil (6)

Uracil (0.091 g, 0.78 mmol) and caesium carbonate (0.169 g, 0.52 mmol) were stirred in dry DMF (40 mL) at room temperature under nitrogen for 30 min. A mixture of 4-bromo- and 4-chloro-1-O-tert-butyldiphenylsilyl-hexanol (0.218 g, ca 0.56 mmol) in dry DMF (2 mL) was added drop-wise. The reaction mixture was heated at 50° C. for 48 h. The crude solution was partitioned between water (10 mL) and EtOAc (10 mL). The organic layer was further washed with brine (2×5 mL), then dried over MgSO$_4$ and concentrated in vacuo to give a transparent oil. This product was further purified by silica gel column chromatography (Isolute SI column) using a gradient elution of 0→5% CH$_3$OH in CHCl$_3$. The fractions with R$_f$=0.03 (30% EtOAc/hexane) afforded the title compound as a transparent oil (0.103 g, ca 41%). A small amount of dialkylated product was isolated as a transparent film (15 mg, ca 3%) from the fractions with R$_f$=0.28 (30% EtOAc/hexane).

$^1$H NMR (300 MHz, CDCl$_3$) δ 1.11 (9H, s, tBu-CH$_3$), 1.41 (4H, m, 3'-H and 4'-H), 1.67 (4H, m, 2'-H and 5'-H), 3.73 (4H, m, 1'-H and 6'-H), 5.76 (1H, dd, J=2.0, 7.9 Hz, 5-H), 7.17 (1H, d, J=7.9 Hz, 6-H), 7.46 (6H, m, Ph-CH), 7.73 (4H, m, Ph-CH), 9.80-9.92 (1H, bm, 3-NH).

$^{13}$C NMR (75 MHz, CDCl$_3$) δ 19.7 (tBu-C), 25.9 (3'-CH$_2$ or 4'-CH$_2$), 26.6 (3'-CH$_2$ or 4'-CH$_2$), 27.3 (tBu-CH$_3$), 29.5 (2'-CH$_2$ or 5'-CH$_2$), 32.8 (2'-CH$_2$ or 5'-CH$_2$), 49.3 (1'-CH$_2$), 64.1 (6'-CH$_2$), 102.5 (5-CH), 128.1 (Ph-CH), 130.0 (Ph-CH), 134.4 (Ph-C), 136.0 (Ph-CH), 144.9 (6-CH), 151.5 (2-C), 164.6 (4-C).

ES$^+$ m/z (%) 473 ([M+Na]$^+$, 100).

HRMS (ES$^+$) Found [M+H]$^+$ 451.2409; C$_{26}$H$_{35}$N$_2$O$_3$Si requires 451.2411.

Example 7

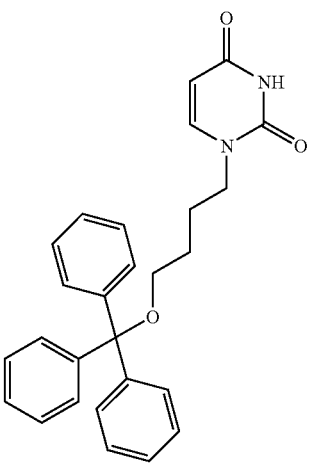

1-(4'-Trityloxybutyl)uracil (7)

1-(4'-Hydroxybutyl)uracil (0.083 g, 0.45 mmol), trityl chloride (0.140 g, 0.50 mmol) and DMAP (5 mg, 0.05 mmol) were stirred in dry pyridine (6 mL) at 50° C. under nitrogen for 64 h. The reaction mixture was left to cool to room temperature and then partitioned between cold water (20 mL) and DCM (15 mL, 2×10 mL). The organic extracts were combined, washed with brine (20 mL), dried over MgSO$_4$ and concentrated in vacuo.

Further purification by silica gel column chromatography (Isolute SI column) using a gradient elution of 0→3% CH$_3$OH in CHCl$_3$. The fractions with R$_f$=0.58 (10% CH$_3$OH/CHCl$_3$) yielded the title compound as a white solid (0.165 g, 86%).

$^1$H NMR (300 MHz, CDCl$_3$) δ 1.27 (2H, m, 3'-H), 1.38 (2H, m, 2'-H), 3.23 (2H, t, J=6.1 Hz, 4'-H), 3.81 (2H, t, J=7.1 Hz, 1'-H), 5.78 (1H, dd, J=2.2, 7.9 Hz, 5-H), 7.18 (1H, d, J=7.9 Hz, 6-H), 7.17-7.56 (15, m, Ph-H), 9.25 (1H, bs, 3-NH).

$^{13}$C NMR (75 MHz, CDCl$_3$) δ 26.5 (2'-CH$_2$), 29.2 (3'-CH$_2$), 49.2 (1'-CH$_2$), 63.0 (4'-CH$_2$), 87.0 (Ph$_3$C), 102.5 (C-5), 127.4 (Ph-CH), 128.3 (Ph-CH), 129.0 (Ph-CH), 144.5 (Ph-C), 144.9 (6-C), 151.2 (2-C), 164.1 (4-C).

2D NMR spectra C—H and NOESY were recorded.

ES$^+$ m/z (%) 449 ([M+Na]$^+$, 40), 55 (100).

HRMS (ES$^+$) Found [M+Na]$^+$ 449.1838. C$_{20}$H$_{14}$N$_2$NaO$_3$ requires 449.1836.

IR (KBr) 3045, 1681 (C=O), 1666 (C=O), 1448, 1074, 760, 706 cm$^{-1}$.

M.p. 68-69° C.

Example 8

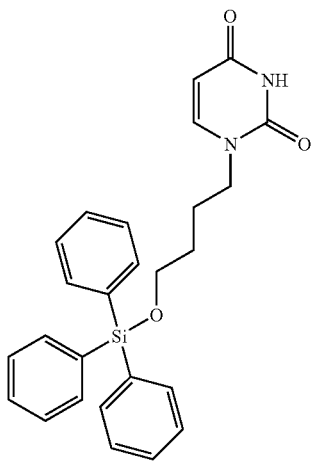

1-(4'-Triphenylsilyloxybutyl)uracil (8)

1-(4'-Hydroxybutyl)uracil (0.048 g, 0.26 mmol) was dissolved in dry pyridine (1.5 mL) and cooled in an ice-salt bath. A solution of triphenylsilyl chloride (0.099 g, 0.34 mmol) in dry pyridine (1.5 mL) was added drop-wise. The reaction mixture was kept at 0° C. under nitrogen for 2 h30. CH$_3$OH (15 µL) was added and after 10 min the solution was concentrated on the rotary evaporator. The resultant crude transparent oil was purified by silica gel chromatography using a gradient elution of 0→3% CH$_3$OH in CHCl$_3$. The title compound was obtained as a white solid (0.085 g, 74%) from the fractions with R$_f$=0.50 (10% CH$_3$OH/CHCl$_3$).

$^1$H NMR (300 MHz, CDCl$_3$) δ 1.65 (2H, m, 3'-H), 1.80 (2H, m, 2'-H), 3.73 (2H, t, J=7.2 Hz, 1'-H), 3.89 (2H, t, J=5.9 Hz, 4'-H), 5.66 (1H, dd, J=1.9, 7.8 Hz, 5-H), 7.02 (1H, d, J=7.8 Hz, 6-H), 7.44 (9H, m, Ph-H), 7.65 (6H, m, Ph-H), 9.59 (1H, bs, 3-NH).

$^{13}$C NMR (75 MHz, CDCl$_3$) δ 26.1 (2'-CH$_2$), 29.4 (3'-CH$_2$), 49.0 (1'-CH$_2$), 63.6 (4'-CH$_2$), 102.5 (5-C), 128.4 (Ph-CH), 130.6 (Ph-CH), 134.4 (Ph-C), 135.8 (Ph-CH), 144.9 (6-C), 151.4 (2-C), 164.4 (4-C).

2D NMR spectra C—H and NOESY were recorded.

ES$^+$ m/z (%) 465 ([M+Na]$^+$, 40), 55 (100).

HRMS (ES$^+$) Found [M+H]$^+$ 443.1787; C$_{26}$H$_{26}$N$_2$O$_3$Si requires 443.1785.

IR (KBr) 3053, 1714 (C=O), 1682 (C=O), 1427, 1117, 703 cm$^{-1}$.

M.p. 131-132° C.

Example 9

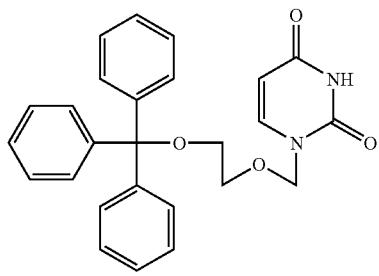

1-(2-Trityloxy-ethoxymethyl)-1H-pyrimidine-2,4-dione 1-(2-hydroxy-ethoxymethyl)uracil (0.50 g, 2.69 mmol) and triphenylmethyl chloride (0.82 g, 2.96 mmol) were stirred in dry pyridine (20 ml) overnight at 50° C. under an atmosphere of nitrogen. H$_2$O (10 ml) was added and the mixture was extracted with CHCl$_3$ (2×50 ml), dried (Na$_2$SO$_4$) and reduced in vacuo to obtain a crude product, which was purified by column chromatography eluting with 0→3% MeOH/CHCl$_3$ to obtain the title compound as a white solid (0.23 g, 20%).

$^1$H NMR (300 MHz; CDCl$_3$): δ 3.32 (2H, 4'-H), 3.78 (2H, m, 5'-H), 5.29 (2H, s, 1'-H), 5.82 (1H, d, J=7.9 Hz, 5-H), 7.29-7.51 (16H, m, Ph-H and 6-H);

$^{13}$C NMR (75 MHz; CDCl$_3$): δ 63.32 (5'-CH$_2$), 69.70 (4'-CH$_2$), 77.38 (1'-CH$_2$), 103.58 (5-CH), 87.19 (Ph$_3$C), 127.55 (Ph-CH), 128.31 (Ph-CH), 129.08 (Ph-CH), 143.25 (Ph-CH), 143.52 (6-CH), 151.43 (2-C), 163.81 (4-C);

MS (ES+ve., m/z): 451.1 (M+Na$^+$, 100%);

HRMS (ES+ve., M+Na$^+$): Calculated for C$_{26}$H$_{24}$N$_2$O$_4$, requires 451.1634, found 451.1626.

IR$_{vmax}$/cm$^{-1}$ (KBr): 703.2 and 760.0 (Aromatic-monosubstituted), 1673.4 (C=O), 1701.8 (C=O), 3021.1 (Aromatic, C—H stretching).

Mp: 145-148° C.

R$_f$ (10% MeOH/CHCl$_3$): 0.71.

Example 10

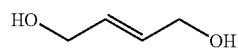

Trans-2-buten-1,4-diol (10)

2-Butyn-1,4-diol (19; 11.64 mmol) was dissolved in dry THF (25 ml) under atmosphere of nitrogen. The solution was cooled to −78° C. with a dry-ice/acetone bath. A cold solution of LAH in THF 1M (12.7 ml; 12.7 mmol) was added with a syringe. The reaction was left worm to room temperature in 4 hours. The disappearance of the starting alkyne was observed by TLC (Hexane/EtOAc 30:70); then the solution was cooled to 0° C. with an ice bath and the quenched with NaOH 1M, until no gas was developed. The pH was adjusted to 8 with HCl 1M and then silica was added to the solution. The solvents were removed under reduced pressure and the residue was loaded into a chromatographic column and purified using Hexane/EtOAc 30:70 as eluent which gave the title compound as a colourless oil (817 mg, 79%). R$_f$: 0.11 in Hexane/EtOAc 30:70 (PMA)

$^1$H-NMR (300 MHz, CD$_3$OD): δ 5.83 (bs; 2H; H-2+H-3); 4.07 (d; J=3.57 Hz; 4H; H-1+H-4)

$^{13}$C-NMR (75 MHz, CD$_3$OD): δ131.7 (C-2 & C-3); 63.4 (C-1 & C-4)

LRMS (ES+): m/z 111.0 [M+Na]$^+$ 100%.

Example 11

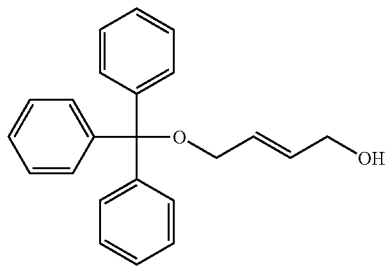

(E)-4-(Trityloxy)but-2-en-1-ol (11)

A solution of Trityl chloride (500 mg; 1.81 mmol), TEA (0.277 ml; 1.99 mmol) and DMAP (8.8 mg; 0.072 mmol) in dry DCM (5 ml) was added with a syringe to a solution of the diol (10) (800 mg; 9.07 mmol) in DCM (15 ml). The mixture was stirred at room temperature for 1 hour and 30 minutes, then other TrCl, TEA and DMAP (half quantities than before) were added. The reaction was stirred at the same temperature until TLC (Hexane/EtOAc 50:50) showed complete disappearance of Trityl chloride. After 1.5 hours water (20 ml) was added and the reaction was stirred for few minutes, then the phases were separated. The organic layer was washed with water (25 ml) and brine (25 ml). The solvent was dried over $MgSO_4$ and evaporated to afford a crude oil which was purified by flash chromatography using Hexane/EtOAc 50:50 as eluent which gave the title compound as a colourless oil, 637 mg, 71%. $R_f$: 0.72 in Hexane/EtOAc 50:50 (UV/PMA).

$^1$H-NMR (300 MHz, $CDCl_3$): δ 7.54-7.51 (m; 6H; H-7); 7.39-7.27 (m; 9H; H-8+H-9); 6.12-6.03 (m; 1H; H-3); 5.91-5.83 (m; 1H; H-2); 4.24 (bs; 2H; H-4); 3.71-3.71 (m; 2H; H-1).

$^{13}$C-NMR (75 MHz, $CDCl_3$): δ 144.6 (C-6); 130.5 (C-3 & C-2); 129.0 (C-8); 128.7 (C-7); 127.4 (C-9); 87.3 (C-5); 64.5 (C-4); 63.8 (C-1).

LRMS (ES+): m/z 331.2 [M+H]+ 100%.

Example 12

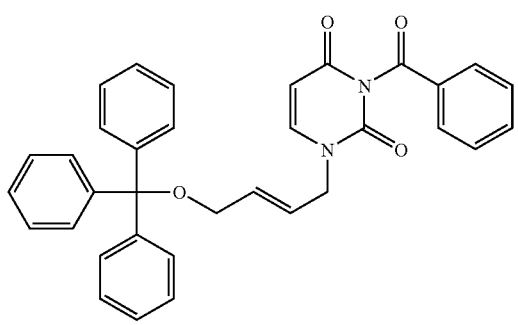

3-Benzoyl-1-[(E)-4-(trityloxy)-2-butenyl]-1,2,3,4-tetrahydro-2,4-pyrimidinedione (12)

Polymer bound triphenylphosphine (0.75 g, 2.25 mmol) was shaken in THF (5 ml) for 15 minutes, then 3-benzoyluracil (290 mg, 1.35 mmol), trityl alcohol (11) (300 mg, 0.90 mmol) were added to the suspension of the resin. A solution of DIAD (0.354 ml, 1.80 mmol) in THF (2 ml) was added to the mixture. The reaction was shaken 24 hours at room temperature and monitored by TLC (Hexane/EtOAc 50:50). The resin was filtered and washed twice with THF (5 ml). The filtrate was concentrated under reduced pressure and taken in EtOAc (5 ml), a white solid precipitated. The precipitate was filtered; the filtrate was concentrated again and purified by flash chromatography using Hexane/EtOAc 40:60→60:40 as gradient which gave the title compound as a white foam (222 mg, 48%). $R_f$: 0.55 in Hexane/EtOAc 50:50 (UV/PMA).

$^1$H-NMR (300 MHz, $CD_3OD$): δ 8.00-7.91 (m; 2H; H-18); 7.74-7.66 (m; 2H; H-6+H-20); 7.56-7.43 (m; 8H; H-13+H-19); 7.34-7.25 (m; 9H; H-14+H-15); 5.94-5.79 (m; 3H; H-5+H-8+H-9); 4.40 (d; J=5.35 Hz; 2H; H-10); 3.71 (bs; 2H; H-7).

$^{13}$C-NMR (75 MHz, $CD_3OD$): δ 174.5 (C-16); 165.1 (C-4); 151.8 (C-2); 147.5 (C-6); 145.9 (C-12); 136.7 (C-17); 134.0 (C-8); 131.8 (C-20); 130.8 (C-19); 130.1 (C-13 & C-18); 129.2 (C-14); 128.6 (C-15); 125.6 (C-9); 102.8 (C-5); 89.2 (C-11); 65.3 (C-10); 51.1 (C-7).

LRMS (Cl+): m/z 546.3 [M+$NH_4$]+ 100%; m/z 529.3 [M+H]+ 45%.

Example 13

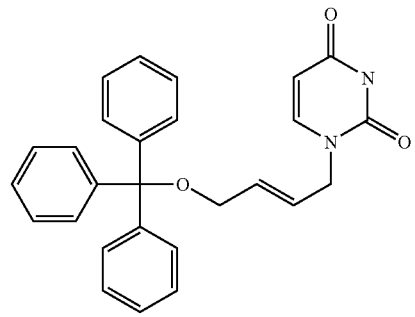

1-[(E)-4-(Trityloxy)-2-butenyl]-1,2,3,4-tetrahydro-2,4-pyrimidinedione (13)

Compound (12) (50 mg, 0.09 mmol) was dissolved and stirred at room temperature in a solution 0.2 M (5 ml) of MeONa in MeOH. The reaction was left at room temperature overnight, then the solution was neutralized with Dowex H+ ion exchange resin. The resin was filtered off and the filtrate was concentrated under reduced pressure to an oil which was purified by chromatography using $CHCl_3$→$CHCl_3$/MeOH 95:5 as gradient which gave the title compound as a white solid (38 mg, 90%). $R_f$: 0.51 in $CHCl_3$/MeOH 90:10, M.p. 70-72° C.

$^1$H-NMR (300 MHz, $CDCl_3$): δ 9.04 (bs; 1H; NH); 7.49 (d; J=7.81 Hz; 6H; H-13); 7.39-7.27 (m; 9H; H-14+H-15); 7.19 (d; J=7.90 Hz; 1H; H-6); 5.98-5.83 (m; 2H; H-8+H-9); 5.77 (d; J=7.90 Hz; 1H; H-5); 4.42 (d; J=5.63 Hz; 2H; H-10); 3.74 (d; J=3.92 Hz; 2H; H-7).

$^{13}$C-NMR (75 MHz, $CDCl_3$): δ 163.9 (C-4); 151.1 (C-2); 144.3 (C-12); 144.1 (C-6); 133.3 (C-8); 129.0 (C-13); 128.3 (C-14); 124.1 (C-15); 124.1 (C-9); 102.9 (C-5); 87.5 (C-11); 64.0 (C-10); 49.6 (C-7).

LRMS (ES+): m/z 447.2 [M+Na]+ 100%.

Microanalysis calculated for $C_{27}H_{24}N_2O_3 \times 0.2H_2O$
C, 75.75; H, 5.74; N, 6.54%. found C, 75.42; H, 5.99; N, 6.22%.

Example 14

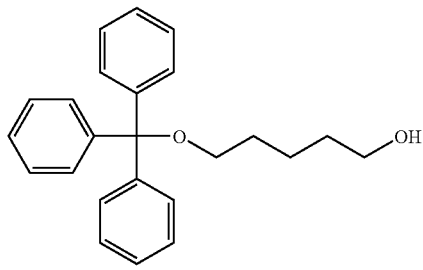

5-Trityloxypentanol (14)

The procedure described in example 1 was followed but using 1,5-pentandiol (376 mg, 3.6 mmol) as alcohol instead of cis-2-buten-1,4-diol, which gave the title compound (300 mg, 24%).

Example 15

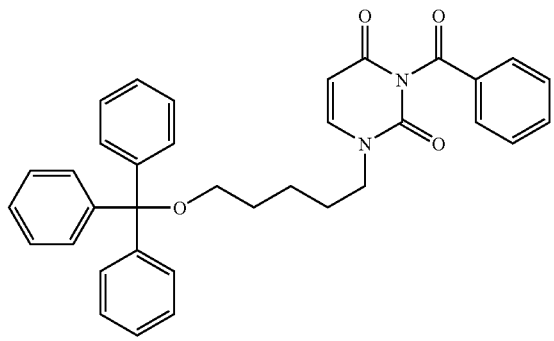

3-Benzoyl-1-(5-trityloxypentyl)-1H-pyrimidine-2,4-dione (15)

Polymer supported triphenyl phosphine (2.5 eq, 3 mmol/g loading) was swelled in dry THF for 15 minutes then the alcohol 14 (1 eq, 300 mg) and the $N^3$-benzoyluracil (1.5 eq) were added into the suspension, which was shaken at room temperature under atmosphere of nitrogen. A solution of DIAD (2 eq) in THF was added slowly into the suspension. The reaction was shaken overnight until the disappearance of the alcohol was observed by TLC. The resin was then filtered off and washed with THF (5 ml). The solvent was removed under reduced pressure to afford a residue which was taken in a mixture of Hexane/EtOAc (50:50). The formed white precipitate was removed and the solution was concentrated to an orange oil and purified by flash chromatography using a mixture of Hexane/EtOAc (40:60) as eluent which gave the title compound (250 mg, 53%).

Example 16

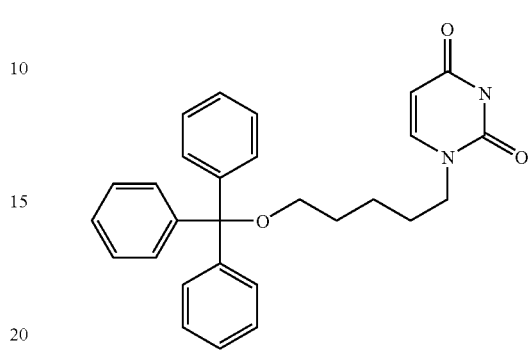

1-[6-(trityloxy)pentyl]-1,2,3,4-tetrahydro-2,4-pyrimidinedione (16)

Compound (15) (231 mg; 0.42 mmol) was stirred for 48 hours at room temperature in a mixture of NaOH 1M and Dioxane 1:1 (8 ml). After 48 hours, Brine (8 ml) was added to the solution, and then extracted with EtOAc (3×8 ml). The organic phase was dried over $MgSO_4$; the solvent was removed in vacuo and the crude residue was purified by flash chromatography using DCM/MeOH 90:10 as eluent. The title compound was obtained as a colourless oil which precipitated after treatment with a mixture of Water/EtOH 1:1 which gave the title compound as a white solid (112 mg, 60%). $R_f$: 0.64 in DCM/MeOH 90:10.

$^1$H-NMR (300 MHz; $CDCl_3$): δ 9.13 (bs; 1H; NH); 7.57-7.55 (m; 6H; H-14); 7.46-7.34 (m; 9H; H-15+H-16), 7.21 (d; J=7.87 Hz; 1H; H-6); 5.80 (d; J=7.87 Hz; 1H; H-5); 3.83 (t; J=7.32 Hz; 2H; H-11); 3.22 (t; J=6.22 Hz; 2H; H-7); 1.84-1.74 (m; 4H; H-10+H-8); 1.60-1.50 (m; 2H; H-9).

$^{13}$C-NMR (75 MHz $CDCl_3$): δ 164.6 (C-4); 151.4 (C-2); 144.9 (C-6); 144.8 (C-13); 129.1 (C-14); 128.4 (C-15); 127.4 (C-16); 102.5 (C-5); 86.9 (C-12); 63.5 (C-11); 49.2 (C-7); 29.9 (C-10); 29.2 (C-8); 23.6 (C-9).

LRMS (ES+): m/z 463.0 [(M+Na)+; 100%].
HRMS (ES+): found 458.2439; required 458.2438 for $C_{28}H_{32}N_3O_3^+$ [M+NH_4]+.

Example 17

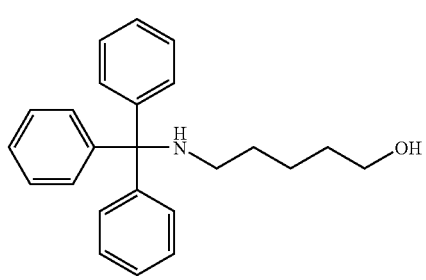

5-(Tritylamino)-pentan-1-ol

The title compound (g, 24%) was prepared as described in example 1 but using 5-aminopentanol instead of cis-2-buten-1,4-diol in the reaction with trityl chloride.

Example 18

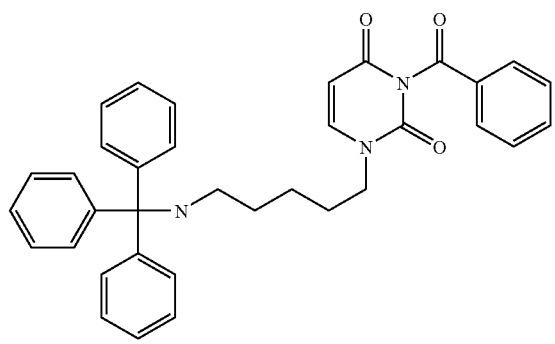

3-Benzoyl-1-[5-(tritylamino)-pentyl]-1H-pyrimidine-2,4-dione (18)

The title compound (187 mg, 53%) was prepared as described in example 15 but using alcohol 17 instead of 14 in the coupling reaction with $N^3$-benzoyluracil.

Example 19

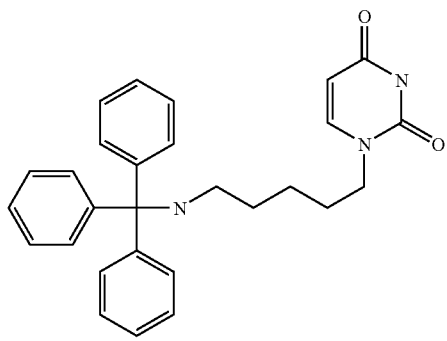

1-[5-(Tritylamino)-pentyl]-1-H-pyrimidine-2,4-dione (19)

Compound 18 (187 mg; 0.35 mmol) was dissolved and stirred in a solution of MeONa 0.2 M in MeOH (17 ml) at room temperature. After 24 hours the pH was adjusted to 7 with Dowex 50WX 8-200 ion exchange resin. The resin was removed by filtration and washed with MeOH. The solution was evaporated and the residue was purified by flash chromatography with DCM/MeOH 90:10 as eluent which gave the title compound as a white foam (240 mg, 52%). $R_f$: 0.50 in DCM/MeOH 90:10.

$^1$H-NMR (300 MHz; CDCl$_3$): δ 8.70 (bs; 1H; N—H); 7.52 (d; J=9.88 Hz; 6H; H-orto); 7.36-7.22 (m; 9H; H-meta+H-para); 7.14 (d; J=7.87 Hz; 1H; H-6); 5.73 (d; J=7.87 Hz; 1H; H-5); 3.74 (t; J=7.32 Hz; 2H; H-7); 2.18 (t; J=7.19 Hz; 2H; H-11); 1.75-1.63 (m; 4H; H-8+H-10); 1.49-1.36 (m; 2H; H-9).

$^{13}$C-NMR (75 MHz CDCl$_3$): δ 163.8 (C-4); 151.0 (C-2); 146.6 (C-13); 144.8 (C-6); 129.0 (C-14); 128.2 (C-15); 126.7 (C-16); 102.5 (C-5); 71.3 (C-12); 49.2 (C-7); 43.7 (C-11); 30.8 (C-8); 29.5 (C-10); 24.6 (C-9).

LRMS (ES+): m/z=262.0 [(M+Na)$^+$; 100%]; m/z=139.9 [(M)$^+$; 50° h]; m/z=243.1 [(Tr)$^+$; 100%].

HRMS (ES+): found 440.2333; required 440.2341 for $C_{28}H_{30}N_3O_2^+$; [M+H]$^+$.

Example 20

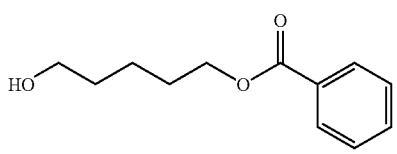

5-hydroxypentyl benzoate (20)

To a solution of pentanediol (1 mmol) in THF (5 ml) was added a catalytic amount of dimethyltin dichloride (0.01 mmol), solid K$_2$CO$_3$ (2.0 mmol) and benzoyl chloride (1.2 mmol), at room temperature. After stirring the mixture at room temperature until the diol disappeared (checked by TLC), the mixture was poured onto water and the organic portion was extracted with DCM. After evaporation of the solvent, a residue was obtained and purified by flash chromatography using a mixture of DCM/MeOH as eluent.

Example 21

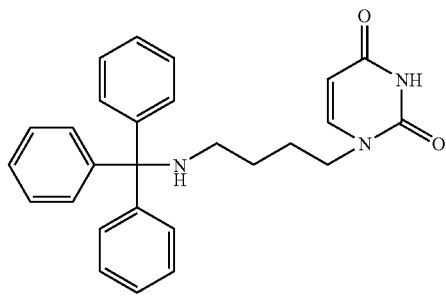

1-(4'-Tritylaminobutyl)uracil (21)

Trityl chloride (0.358 g, 1.28 mmol) was added to a solution of 1-(4'-aminobutyl)uracil (contaminated by 11% 1,3-bis (4'-aminobutyl)uracil) (0.168 g) in anhydrous pyridine (15 mL). The reaction mixture was heated at 50° C. for 44 h, left to cool to room temperature, poured into cold water (50 mL) and extracted with DCM (3×25 mL). The organic extracts were washed with brine (40 mL), dried over Na$_2$SO$_4$ and concentrated in vacuo. Further purification was carried out by silica gel column chromatography, using Jones Chromatography Isolute SI columns with a gradient elution of 0→5% CH$_3$OH in CHCl$_3$. The fractions with $R_f$=0.51 (10% CH$_3$OH/CHCl$_3$) gave the title compound as a white crystalline solid (94 mg, ca 24%).

¹H NMR (300 MHz, CDCl₃) δ 1.58 (3H, m, 3',5'-H), 1.80 (2H, m, 2'-H), 2.23 (2H, t, J=6.7 Hz 4'-H), 3.75 (2H, t, J=7.2 Hz, 1'-H), 5.73 (1H, d, J=7.9 Hz, 5-H), 7.13 (1H, d, J=7.9 Hz, 6-H), 7.19-7.40 (9H, m, Ph-H), 7.53 (6H, m, Ph-H), 8.53 (1H, bs, 3-NH).
¹³C NMR (75 MHz, CDCl₃) δ 27.3 (2'-CH₂), 28.1 (3'-CH₂), 43.5 (4'-CH₂), 49.3 (1'-CH₂), 71.3 (6'-C), 102.5 (5-CH), 126.7 (Ph-CH), 128.3 (Ph-CH), 129.0 (Ph-CH), 144.8 (6-CH), 145.5 (Ph-C), 151.0 (2-C), 163.7 (4-C).
2D NMR spectra H—H, C—H and NOESY were recorded.
ES⁺ m/z (%) 426 ([M+H]⁺, 18), 243 (PhC⁺, 100).
HRMS (ES⁺) Found [M+H]⁺ 426.2176; $C_{27}H_{28}N_3O_2^+$ requires 426.2176.
IR (KBr) 3054, 1694, 1672, 1454, 768, 706 cm⁻¹.
M.p. 219-220° C. (dec.).
Anal (%) found C, 73.10; H, 6.12; N, 9.45; Cl, 3.61.
Calcd for $C_{27}H_{27}N_3O_2$, 0.48 HCl C, 73.20; H, 6.25; N, 9.48; Cl, 3.84.

Example 22

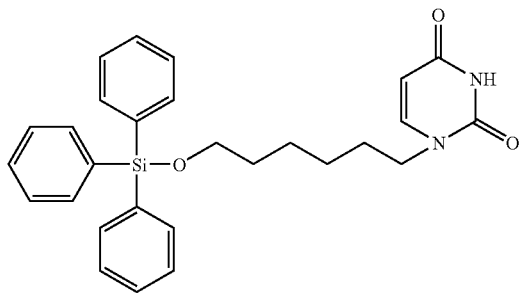

1-(6'-Triphenylsilyloxyhexyl)uracil (22)

A solution of triphenylsilyl chloride (0.337 g, 1.14 mmol) in dry pyridine (3 mL) was added drop-wise to a solution of 1-(6'-hydroxyhexyl)uracil (0.200 g, 0.94 mmol) in dry pyridine (4 mL) cooled in an ice-salt bath. The reaction mixture was kept at 0° C. under nitrogen for 3 h30. As TLC monitoring evidenced the presence of unreacted starting material, triphenylsilyl chloride (0.325 g, 1.10 mmol) in dry pyridine (1 mL) was added. After a further 45 min at 0° C., the reaction had reached completion and was quenched with CH₃OH (0.1 mL). Removal of the solvent in vacuo afforded a crude yellow oil which was purified by silica gel chromatography using a Jones Chromatography Isolute SI column with a gradient elution of 0→5% CH₃OH in CHCl₃. The title compound was obtained as a white solid (0.140 g, 32%) from the fractions with $R_f$=0.52 (10% CH₃OH/CHCl₃). Some starting material (0.130 g, 65%) was also recovered, possibly resulting from hydrolysis during the work up.
¹H NMR (300 MHz, CDCl₃) δ 1.29-1.53 (4H, m, 3',4'-H), 1.67 (4H, m, 2',5'-H), 3.72 (2H, t, J=7.3 Hz, 1'-H), 3.88 (2H, t, J=6.3 Hz, 6'-H), 5.74 (1H, d, J=7.8 Hz, 5-H), 7.12 (1H, d, J=7.8 Hz, 6-H), 7.47 (9H, m, Ph-H), 7.70 (6H, m, Ph-H), 9.83 (1H, bs, 3-NH).
¹³C NMR (75 MHz, CDCl₃) δ 25.8 (3'-CH₂ or 4'-CH₂), 26.5 (4'-CH₂ or 3'-CH₂), 29.4 (2'-CH₂), 32.7 (5'-CH₂), 49.2 (1'-CH₂), 64.1 (6'-CH₂), 102.5 (5-CH), 128.3 (Ph-CH), 130.5 (Ph-CH), 134.8 (Ph-C), 135.8 (Ph-CH), 144.9 (6-CH), 151.4 (2-C), 164.5 (4-C).
ES⁺ m/z (%) 493 ([M+Na]⁺, 13).
HRMS (ES⁺) Found [M+H]⁺ 471.2100; $C_{28}H_{31}N_2O_3Si^+$ requires 471.2098.

IR (KBr) 3050, 2938, 2870, 1698, 1666, 1428, 1117, 700, 503 cm⁻¹.
M.p. 140-141° C.
Anal (%) found C, 70.48; H, 6.42; N, 5.88; Cl, 1.26.
Calcd for $C_{28}H_{30}N_2O_3Si$, 0.18 HCl C, 70.47; H, 6.37; N, 5.87; Cl, 1.34.

Example 23

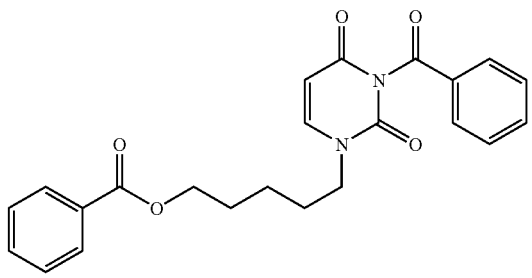

Benzoic acid 5-(3-benzoyl-2,4-dioxo-3,4-dihydro-2H-pyrimidin-1-yl)-pentyl ester (23)

The title compound (50%) was prepared as described in example 15 but using the alcohol 20 instead of 14 in the coupling reaction with N³-benzoyluracil.

Example 24

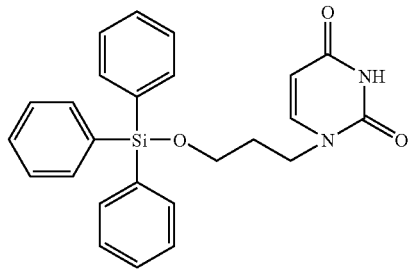

1-(3'-Triphenylsilyloxypropyl)uracil (24)

1-(3'-hydroxypropyl)uracil (0.193 g, 1.134 mmol) was dissolved in dry pyridine (4 mL) and cooled in an ice-salt bath. A solution of triphenylsilyl chloride (0.432 g, 1.46 mmol) in dry pyridine (3 mL) was added drop-wise. The reaction mixture was kept at 0° C. under nitrogen for 4 h30. As TLC monitoring evidenced the presence of unreacted starting material, more triphenyl silyl chloride (0.204 g, 0.69 mmol) in dry pyridine (1 mL) was added. After a further 15 min at 0° C., the reaction had reached completion and was quenched with CH₃OH (50 μL). Removal of the solvent in vacuo afforded a crude yellow oil which was purified by silica gel chromatography, using a Jones Chromatography Isolute SI column eluted with a gradient of 0→5% CH₃OH in CHCl₃. The title compound was obtained as a white solid (0.392 g, 81%) from the fractions with $R_f$=0.52 (10% CH₃OH/CHCl₃). Some compound starting material was also recovered (34 mg, 18%).
¹H NMR (300 MHz, CDCl₃) δ 2.01 (2H, m, 2'-H), 3.94 (4H, m, 1',3'-H), 5.54 (1H, d, J=7.9 Hz, 5-H), 7.04 (1H, d, J=7.9 Hz, 6-H), 7.51 (9H, m, Ph-H), 7.68 (6H, m, Ph-H), 9.49 (1H, bs, 3-NH).

$^{13}$C NMR (75 MHz, CDCl$_3$) δ 31.5 (2'-CH$_2$), 32.7 (5'-CH$_2$), 46.4 (1'-CH$_2$), 60.3 (6'-CH$_2$), 102.1 (5-CH), 128.3 (Ph-CH), 130.8 (Ph-CH), 134.0 (Ph-C), 135.8 (Ph-CH), 145.6 (6-CH), 151.3 (2-C), 164.3 (4-C).

ES$^+$ m/z (%) 879 ([2M+Na]$^+$, 8), 451 ([M+Na]$^+$, 38), 87 (100).

HRMS (ES$^+$) Found [M+NH$_4$]$^+$ 446.1844; C$_{27}$H$_{28}$N$_3$O$_4$Si$^+$ requires 446.1844. M.p. 150-151° C.

Example 25

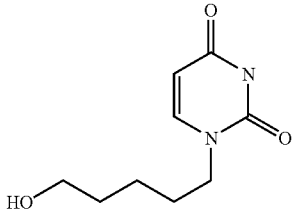

1-(5-Hydroxypentyl)-1H-pyrimidine-2,4-dione (25)

The benzoyl groups of compound 23 were removed according to the procedure described in example 16 which gave the title compound (50 mg, 50%).

Example 26

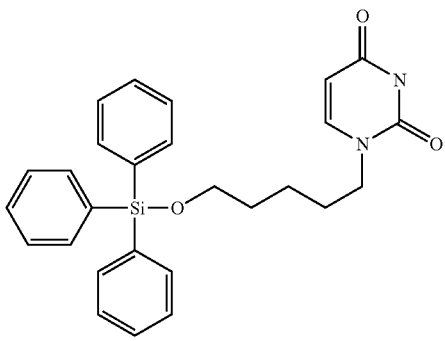

1-(5-Triphenylsilanyloxypentyl)-1H-pyrimidine-2,4-dione (26)

A solution of triphenylsilyl chloride (81 mg; 0.27 mmol) in pyridine (1 ml) was added to a solution of alcohol (25) (50 mg; 0.25 mmol) in dry Pyridine (1 ml) under atmosphere of nitrogen, at room temperature.

The reaction was left stirring at 25° C. 24 hours, and then the solvent was removed under reduced pressure. The residue a slightly yellow oil was purified by chromatography using DCM/MeOH 99:1 as eluent.

Light orange syrup, 30 mg; 26%. Rf: 0.69 in DCM/MeOH 95:5

$^1$H-NMR (300 MHz; CDCl$_3$): δ 9.26 (s; 1H; NH); 7.68-7.65 (m; 6H; H-13); 7.54-7.43 (m; 9H; H-14+H-15); 7.08 (d; J=7.87 Hz; 1H; H-6); 5.69 (d; J=7.87 Hz; 1H; H-5); 3.87 (t; J=6.13 Hz; 2H; H-7); 3.72 (t; J=7.30 Hz; 2H; H-11); 1.76-1.66 (m; 4H; H-10+H-8); 1.51-1.43 (m; 2H; H-9).

$^{13}$C-NMR (75 MHz; CDCl$_3$): δ 164.2 (C-4); 151.2 (C-2); 144.9 (C-6); 136.4 (C-13); 134.4 (C-14); 130.5 (C-15); 128.7 (C-12); 102.4 (C-5); 63.8 (C-11); 49.2 (C-7); 32.2 (C-10); 29.0 (C-8); 23.2 (C-9).

LRMS (ES+): m/z 479.0 [(M+Na), 100%].

HRMS (ES+): found 479.1780; required 479.1761 for CH$_{27}$H$_{28}$N$_2$SiO$_3^+$; [M+Na]$^+$.

Microanalysis calculated for C$_{27}$H$_{28}$N$_2$O+ 0.6H$_2$O: C, 69.4; H, 6.30; N, 5.99%. found C, 69.79; H, 6.26; N, 5.45%.

Example 27

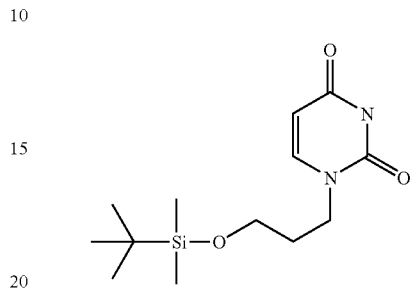

1-[3-(tert-Butyl-dimethyl-silanyloxy)-propyl]-1H-pyrimidine-2,4-dione (27)

3-bromo-1-tetrabutyldimethylsilyl propanol (641 mg, 2.68 mmol) was added into a solution of uracil (300 mg, 2.68 mmol) and cesium carbonate Cs$_2$CO$_3$ (872 mg, 2.68 mmol) in DMF (10 ml), under N$_2$. The reaction was warmed to 60° C. for 4 hours, until the TLC (EtOAc/Hexane 3:1) showed the complete disappear of the starting material. Water (10 ml) was added, and the mixture was extracted with EtOAc (3×10 ml), dried and evaporated the solvent under reduced pressure. The obtained residue (a colourless oil) was purified by flash chromatography using a mixture of EtOAc/Hexane as eluent which gave the title compound (250 mg, 33%).

$^1$H-NMR (300 MHz; CDCl$_3$) δ: 9.15 (bs; 1H; N—H); 7.30 (d; J=7.87 Hz; 1H; H-6); 5.72 (d; J=7.87 Hz; 1H; H-5); 3.91 (t; J=6.58 Hz; 2H; H-9); 3.70 (t; J=6.58 Hz; 2H; H-7); 1.94 (q; J=6.58 Hz; 2H; H-8); 0.95 (s; 9H; H-11); 0.00 (s; 6H; H-10).

$^{13}$C-NMR (75 MHz; CDCl$_3$) δ: 164.3 (C-4); 151.2 (C-2); 102.0 (C-5); 59.4 (C-9); 46.6 (C-7); 31.6 (C-8); 26.3 (C-11); 18.6 (C-12); -5.0 (C-10).

LRMS (ES+) m/z: 307.2 [(M+Na)$^+$, 100%].

Example 28

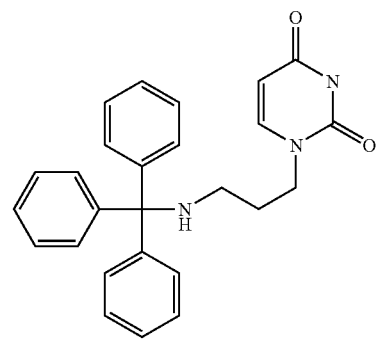

1-(3'-Tritylaminopropyl)uracil (28)

Uracil (0.230 g, 2.05 mmol) was stirred with Cs$_2$CO$_3$ (0.462 g, 1.42 mmol) in DMF (8 mL) at room temperature for 30 min. A solution of 3-bromo-1-tritylpropylamine (0.507 g, 1.33 mmol) in DMF (3 mL) was then added dropwise. The reaction mixture was heated at 40° C. under nitrogen for 58 h, left to cool to room temperature, poured into cold water (20 mL) and extracted with EtOAc (25 mL). The organic extracts were washed with brine, dried over $Na_2SO_4$ and concentrated in vacuo. Further purification was carried out by flash column chromatography performed using a ISOLUTE SI column eluted with 20→50% EtOAc in hexane. The fractions with $R_f$=0.38 (20% EtOAc/hexane) gave the title compound slightly contaminated with DMF as a white solid (0.203 g, app. 37%). To remove the remaining traces of DMF, the compound was chromatographed again, this time using a 0-10% $CH_3OH$ in $CHCl_3$ as eluent. The title compound was isolated (0.116 g, 21%).

$^1$H NMR (300 MHz, $CDCl_3$+$CD_3OD$) δ 1.87 (2H, m, 2'-H), 2.20 (2H, t, J=6.5 Hz, 3'-H), 3.85 (2H, t, J=7.2 Hz, 1'-H), 5.61 (1H, d, J=7.9 Hz, 5-H), 7.09 (1H, d, J=7.9 Hz, 6-H), 7.15-7.35 (9H, m, 5",6"-H), 7.47 (6H, m, 4"-H).

$^{13}$C NMR (75 MHz, $CDCl_3$+$CD_3OD$) δ 30.3 (2'-$CH_2$), 40.4 (3'-$CH_2$), 47.2 (1'-$CH_2$), 71.2 (2"-C), 102.4 (5-CH), 126.8 (6"-CH), 128.3 (5"-CH), 129.0 (4"-CH), 144.9 (6-CH), 146.1 (3"-C), 151.4 (2-C), 164.8 (4-C).

ES$^+$ m/z (%) 845 ([2M+Na]$^+$, 3), 434 ([M+Na]$^+$, 22), 412 ([M+H]$^+$, 10), 243 (PhC$^+$, 42).

HRMS (ES$^+$) Found [M+H]$^+$ 412.2018; $C_{26}H_{26}N_3O_2^+$ requires 412.2020.

M.p. 228-230° C. (dec.).

Anal calcd for $C_{26}H_{25}N_3O_2$, 0.19(%): HBr C, 73.16; H, 5.95; N, 9.84; Br, 3.56 found: C, 73.17, H, 6.11, N, 9.78; Br, 4.91.

Example 29

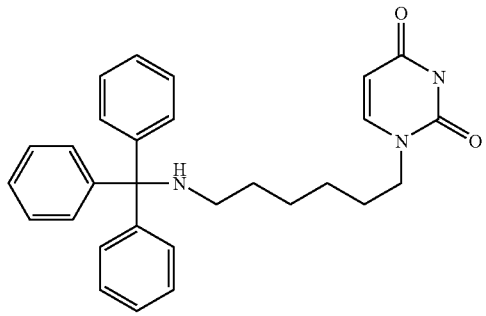

1-(6'-Tritylaminohexyl)uracil (29)

Uracil (0.087 g, 0.776 mmol) was stirred with $Cs_2CO_3$ (0.169 g, 0.519 mmol) in DMF (4 mL) at room temperature for 1 h. A solution of O-tosyl-6-tritylaminohexanol (0.250 g, 0.487 mmol) in DMF (2 mL) was then added dropwise. The reaction mixture was heated at 40° C. for 64 h, left to cool to room temperature, poured into cold water (15 mL) and extracted with EtOAc (25 mL). The organic extracts were washed with brine (10 mL), dried over $Na_2SO_4$ and concentrated in vacuo. Further purification was carried out by flash column chromatography (ISOLUTE SI column) using a gradient elution of 20→50% EtOAc in hexane. The fractions with $R_f$=0.49 (10% $CH_3OH/CHCl_3$) gave the title compound slightly contaminated with DMF as a white solid (0.111 g, ca 50%). Remaining traces of DMF could be removed by recrystallisation from $CH_3OH$ or alternatively by water wash with a purification yield of 70-80%.

$^1$H NMR (300 MHz, $CDCl_3$) δ 1.25-1.85 (9H, m, 2',3',4', 5'-H and 1"-NH), 2.17 (2H, t, J=6.8 Hz, 6'-H), 3.74 (2H, t, J=7.4 Hz, 1'-H), 5.73 (1H, d, J=7.9 Hz, 5-H), 7.16 (1H, d, J=7.9 Hz, 6-H), 7.20-7.65 (9H, m, 5",6"-H), 7.53 (6H, m, 4"-H).

$^{13}$C NMR (75 MHz, $CDCl_3$) δ26.8 ($CH_2$), 27.3 ($CH_2$), 29.4 ($CH_2$), 31.1 ($CH_2$), 43.8 (6'-$CH_2$), 49.3 (1'-$CH_2$), 71.3 (2"-C), 102.4 (5-CH), 126.6 (6"-CH), 1282 (5"-CH), 129.1 (4"-CH), 144.8 (6-CH), 146.7 (3"-C), 151.2 (2-C), 164.2 (4-C).

ES$^+$ m/z (%) 929 ([2M+Na]$^+$, 7), 907 ([2M+H]$^+$, 8), 476 ([M+Na]$^+$, 30), 454 ([M+H]$^+$, 46), 243 (PhC$^+$, 100).

HRMS (ES$^+$) Found [M+H]$^+$ 454.2490; $C_{29}H_{32}N_3O_2^+$ requires 454.2489.

M.p. 156-157° C.

Anal calcd for (%): $C_{29}H_{31}N_3O_2$, C, 76.79; H, 6.89; N, 9.26. found: C, 76.61; H, 6.89; N, 9.19.

Example 30

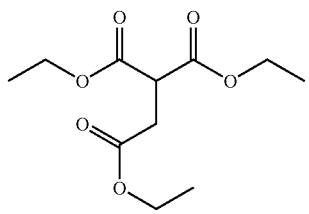

2-Ethoxycarbonyl-succinic acid diethyl ester (30)

A suspension of NaH (60%, 90 g, 3.75 mol) in dry THF (7.5 L) was cooled to 0° C. and to this was added a solution of diethylmalonate (500 g, 3.12 mol) over a period of 1 h. The reaction mixture was slowly allowed to warm to RT and stirred for another 1.5 h at RT. The reaction mixture was then cooled to 0° C. and added a solution of ethylbromoacetate (307 mL, 2.79 mol) slowly for 30 min and finally stirred at RT for 2.5 h. The reaction mixture is poured into a mixture of 1.5 N HCl (250 mL) and ice (5 kg), extracted with $CH_2Cl_2$ (4×5 L), dried and concentrated under vacuum to give crude product. The crude was purified by column chromatography over silica gel (4% ethyl acetate in pet. ether) to give the title compound (496 g, 64%). TLC: Pet. ether/EtOAc, 4:1, $R_f$=0.4

Example 31

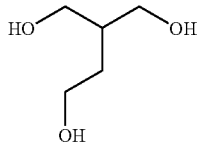

2-Hydroxymethylbutane-1,4-diol (31)

To a solution of compound 30 (495 g, 2.01 mol) in tert-butanol (4 L) was added $NaBH_4$ (434 g, 12.04 mol) with vigorous stirring at RT under $N_2$ atmosphere. To this stirred solution was added methanol (250 mL) in three portions during 45 mins maintaining a gentle reflux. The reaction mixture was slowly warmed to 80° C. and allowed to reflux at the same temperature for over night. The reaction mixture was cooled, added 5M hydrochloric acid to get pH=7 (app). The mixture was filtered, the residue washed with ethanol (2×500 mL) and combined the organic layers. The solvent was removed under vacuum and the crude product was purified by column chromatography on silica gel (10% methanol in chloroform) to give the title compound (160 g, 66%). TLC: Chloroform/Methanol, 4:1, $R_f$=0.2

Example 32

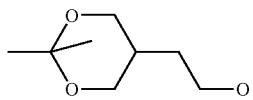

2-(2,2-Dimethyl-[1,3]dioxan-5-yl)-ethanol (32)

A solution of compound 31 (160 g, 1.30 mol) and 2,2'-dimethoxypropane (207 g, 1.90 mol) in dry acetone (800 mL) was added p-TsOH (92 g, 0.053 mol) under $N_2$ and stirred at RT for 12 h. To this was added triethylamine drop-wise to neutral pH and then concentrated under vacuum below 35° C. The crude residue was purified by column chromatography over neutral alumina (12% ethyl acetate in pet ether) to give the title compound (84 g, 39%). TLC: Pet ether/EtOAc, 1:1, $R_f$=0.2

Example 33

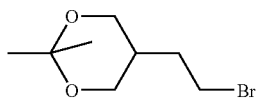

5-(2-Bromoethyl)-2,2-dimethyl-[1,3]dioxane (33)

To a solution of compound 32 (84 g, 0.528 mol) in dry DMF (500 mL) was added triphenylphosphine (207 g, 0.79 mol) with vigorous stirring until it becomes a clear solution. The mature was cooled to 0° C. and added $CBr_4$ (260 g, 0.79 mol) portion wise over a period of 30 min and allowed to stir at RT for 5 h. The reaction mixture was cooled to 0° C., added saturated $NaHCO_3$ solution (200 mL) and extracted with hexane (4×200 mL). The combined organic layer was dried, concentrated under vacuum and the crude title compound (117 g) was used for next reaction without any purification. TLC: Pet. ether/EtOAc, 7:3, $R_f$=0.6

Example 34

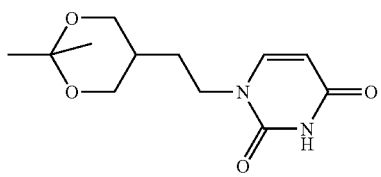

1-[2-(2,2-Dimethyl-[1,3]dioxan-5-yl)-ethyl]-1H-pyrimidine-2,4-dione (34)

To a solution of uracil (88.5 g, 0.79 mol) in dry DMF (250 mL) was added cesium carbonate (171 g, 0.527 mol) at RT and stirred at the same temperature for 30 min. To the above reaction mixture was added a solution of compound 33 (117 g, 0.527 mol) in dry DMF (250 mL) over a period of 30 min and heated at 50° C. for 24 h. The reaction mixture was filtered, filtrate concentrated under vacuum and crude purified by column chromatography over silica gel (3% methanol in chloroform) to give the title compound (60 g, 45%). TLC: Chloroform/Methanol, 4:1, $R_f$=0.3

Example 35

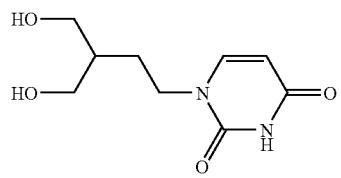

1-(4-Hydroxy-3-hydroxymethylbutyl)-1H-pyrimidine-2,4-dione (35)

A mixture of compound 34 (60 g, 0.239 mol) in 1N HCl (450 mL) was heated to 110° C. for 30 min. The reaction mixture was cooled, carefully neutralized with potassium carbonate to pH=7 and concentrated under vacuum. The residue was passed through small column using 20% methanol in chloroform to give the title compound (45 g, 88%) as a thick liquid. TLC: Chloroform/Methanol, 6:4, $R_f$=0.2

Example 36

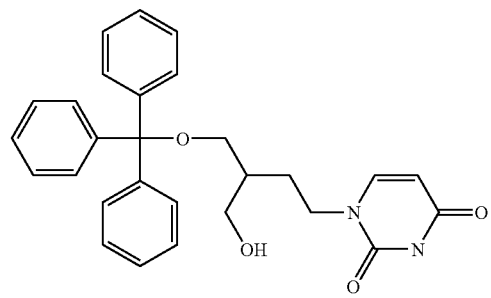

1-(3-Hydroxymethyl-4-trityloxybutyl)-1H-pyrimidine-2,4-dione (36)

To a solution of compound 35 (45 g, 0.213 mol) in dry DMF (225 mL) was added triethylamine (60 mL, 0.425 mol) and stirred at RT for 15 min. The above reaction mixture was cooled to 0° C., added tritylchloride (59 g, 0.213 mol) followed by addition of catalytic amount of 4-DMAP (app. 20 mg) and allowed to stir at RT for 24 h. The reaction was diluted with water (100 mL), extracted with ethyl acetate (5×200 mL), dried and concentrated under vacuum. The crude was purified by column chromatography over silica gel (6% methanol in chloroform) to give the title compound (33 g, 34%). TLC: Chloroform/Methanol, 9:1, $R_f$=0.5

Example 37

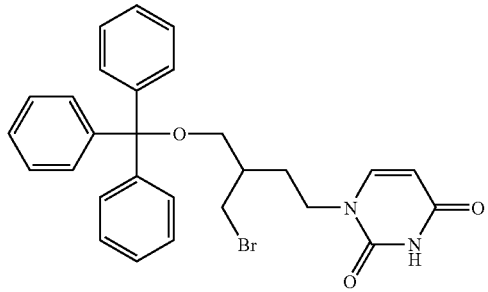

1-(3-Bromomethyl-4-trityloxybutyl)-1H-pyrimidine-2,4-dione (37)

To a solution of compound 36 (33 g, 0.073 mol) in dry DMF (200 mL) was added triphenylphosphine (29 g, 0.11 mol) with vigorous stirring at RT. The reaction mixture was cooled to 0° C., added CBr$_4$ (36 g, 0.11 mol) portionwise over a period of 30 min and allowed to stir at RT for 24 h. The reaction mixture was cooled to 0° C., added saturated NaHCO$_3$ solution (100 mL) and extracted with ethyl acetate (4×150 mL). The combined organic layer was dried, concentrated under vacuum and the crude product was purified by column chromatography on silica gel (50% ethyl acetate in hexane) to give the title compound (22 g, 57%). TLC: 100% EtOAc, $R_f$=0.7

Example 38

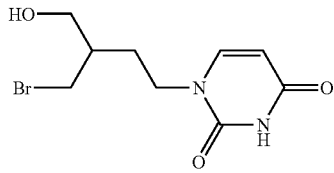

1-(3-Bromomethyl 4-hydroxybutyl)-1H-pyrimidine-2,4-dione (38)

A solution of compound 37 (22 g, 0.042 mol) in methanol (100 mL) was treated with PTSA. H$_2$O (0.80 g, 0.0042 mol) and stirred for 6 h at RT. The reaction mixture was concentrated under vacuum and the crude compound was used for next reaction (10.5 g, crude product). TLC: Chloroform/Methanol, 1:1, $R_f$=0.2

Example 39

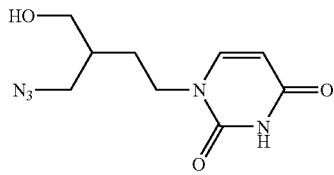

1-(3-Azidomethyl-4-hydroxybutyl)-1H-pyrimidine-2,4-dione (39)

A solution of compound 38 (10.9 g, 0.042 mol) in dry DMF (40 mL) was treated with NaN$_3$ (4.1 g, 0.062 mol) and heated to 70° C. for 24 h. The reaction mixture was concentrated under vacuum and crude purified by column chromatography over silica gel (30% methanol in chloroform) to give the title compound (5.2 g, 47%). TLC: Chloroform/Methanol, 1:1, $R_f$=0.2

Example 40

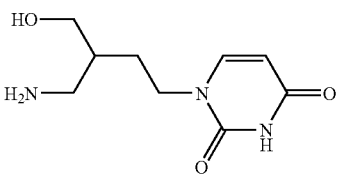

1-(3-Aminomethyl-4-hydroxylbutyl)-1H-pyrimidine-2,4-dione (40)

A mixture of compound J (5.2 g, 0.022 mol) in dry methanol (50 mL) was treated with triethylamine (15 mL, 0.108 mol) and 1,3-propanedithiol (3.5 ml, 0.032 mol) at RT and allowed to stir for 24 h. The reaction mixture was followed by TLC and further added same amount of triethylamine and 1,3-propanedithiol. The reaction was continued for another 24 h and filtered off the solid. The filtrate was concentrated under vacuum and the residue was treated with ethyl acetate. The solid was filtered off and dried and the crude title compound (4 g, 86%) was used in the next step without any purification. TLC: Chloroform/Methanol, 1:4, $R_f$=0.1

Example 41

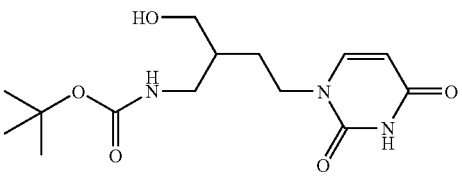

[4-(2,4-Dioxo-3,4-dihydro-2H-pyrimidin-1-yl)-2-hydroxymethylbutyl]-carbamic acid tert-butyl ester (41)

To a solution of compound 40 (4 g, 0.0187 mol) in THF/water (30 mL, 1:1) was added NaHCO$_3$ (1.9 g, 0.0225 mol) at 0° C., followed by addition of Boc$_2$O (4.9 mL, 0.0225 mol) and was stirred at RT for 12 h. The reaction mixture was concentrated under vacuum and the residue was extracted with ethyl acetate (3×25 mL). The combined organic layers were washed with brine, dried, concentrated and the crude product was purified by column chromatography on silica gel (10% methanol in chloroform) to give the title compound (4.6 g, 78%). TLC: Chloroform/Methanol, 4:1, $R_f$=0.6

Example 42

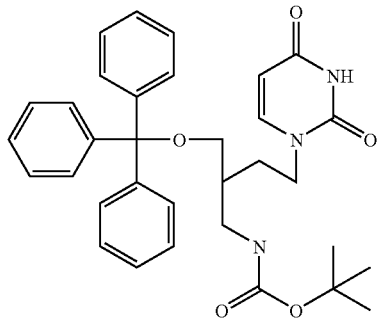

[4-(2,4-Dioxo-3,4-dihydro-2H-pyrimidin-1-yl)-2-trityloxymethylbutyl]-carbamic acid tert-butyl ester (42)

A glass tube for microwave was charged with compound 41 (50 mg; 0.155 mmol), trityl chloride (54 mg; 0.19 mmol) and dry pyridine (2 ml). The tube was sealed with a septum cap. The vial was irradiated with MW to reach the temperature of 160° C. for 5 minutes. The irradiating cycle was repeated 3 times, and then the mixture was poured into a round bottom flask. The solvent was removed under reduced pressure and the crude was purified by chromatography using Hexane/EtOAc 40:60 as eluent which gave the title product as a white foam (70 mg, 79%). $R_f$: 0.27 in Hexane/EtOAc 40:60, M.p: 86-88° C.

$^1$H-NMR (300 MHz, CDCl$_3$): δ 8.08 (bs; 1H; NH): 7.48 (d; J=7.04 Hz; 6H; H-14); 7.40-7.27 (m; 10H; H-6+H-15+H-16); 5.67 (dd; J$_1$=7.90 Hz; J$_2$=2.35 Hz; 1H; H-5); 4.58 (t; J=6.13 Hz; 1H; NHBoc); 3.84-3.76 (m; 2H; H-10); 3.31-323 (m; 3H; H-7+1 of H-11); 3.10-3.05 (m; 1H; 1 of H-11); 1.85-1.67 (m; 2H; H-8); 1.62-1.53 (m; 1H; H-9); 1.47 (s; 9H; H-19).

LRMS (Cl+): m/z 243.2 [Trt]$^+$ 100%.

Microanalysis calculated for $C_{33}H_{37}N_3O_5 \times 0.2H_2O$

C, 70.87; H, 6.74; N, 7.51%. found C, 70.86; H, 7.13; N, 6.98%.

Example 43

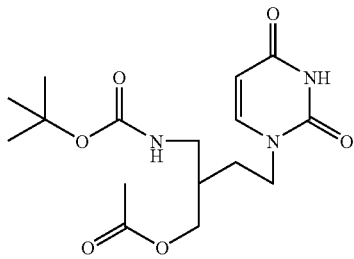

Acetic acid 2-(tert-butoxycarbonylaminomethyl)-4-(2,4-dioxo-3,4-dihydro-2H-pyrimidi-1-yl)-butyl ester (43)

Alcohol 41 (200 mg, 64 mmol) was dissolved in a solution of acetic anhydride:pyridine 1:2 (15 ml) and the solution was stirred at room temperature for 3 h. The solution was then evaporated in vacuo and the afforded residue was purified by column chromatography on silica gel which gave the title compound (205 mg, 90%).

Example 44

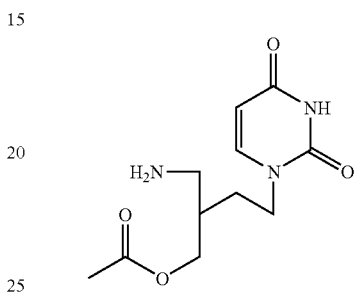

Acetic acid 2-aminoethyl(2,4-dioxo-3,4-dihydro-2H-pyrimidin-1-yl)-butyl ester (44)

TFA (2 ml) was added to a solution of compound 43 (200 mg, 0.56 mmol) in dichloromethane (4 ml). The solution was stirred at room temperature for 30 min where after the solvents were evaporated in vacuo which gave the title compound as the TFA salt.

Example 45

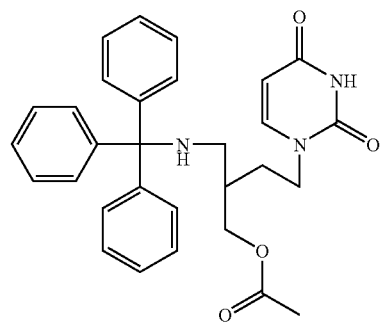

Acetic acid 4-(2,4-dioxo-3,4-dihydro-2H-pyrimidin-1-yl)-[(tritylamino)methyl]-butyl ester (45)

Trityl chloride (128 mg, 0.46 mmol) was added to a solution of (44) (100 mg, 0.43 mmol) in dry DCM (5 ml) in presence of TEA (0.64 ml, 0.46 mmol). The reaction was stirred at room temperature. After six hours the TLC (DCM/MeOH 90:10) showed still presence of starting material, then some more TrCl (0.5 eq.) and TEA (0.5 eq.) were added. The reaction was left stirring overnight. Water (5 ml) was added and the mixture was stirred other 5 minutes. The phases were separated and the organic phase was washed with HCl 0.1 M (5 ml). The organic layer was dried over MgSO$_4$, concentrated and purified by flash chromatography using DCM→DCM/MeOH 95:5 as gradient which gave the title product as a white solid (150 mg, 70%). R$_f$: 0.60 in CHCl$_3$/MeOH 90:10

$^1$H-NMR (300 MHz, CDCl$_3$): δ 9.07 (bs; 1H; NH); 7.46 (d; J=7.34 Hz; 6H; H-16); 7.30-7.19 (m; 9H; H-17+H-18); 7.02 (d; J=7.88 Hz; 1H; H-6); 5.66 (d; J=7.88 Hz; 1H; H-5); 4.27 (d; J=5.00 Hz; 2H; H-10); 3.68 (m; 2H; H-7); 2.17 (d; J=6.02; 2H; H-11); 2.03 (s; 3H; H-12); 1.83-1.65 (m; 3H; H-9+H-8).

$^{13}$C-NMR (75 MHz, CDCl$_3$): δ 171.5 (C-12); 1640 (C-4); 151.1 (C-2); 146.2 (C-15); 144.7 (C-6); 129.0 (C-16); 128.3 (C-17); 126. (C-18); 102.7 (C-5); 71.3 (C-14); 65.3 (C-10); 47.4 (C-7); 44.6 (C-11); 37.0 (C-9); 29.7 (C-8).

LRMS (CI+): m/z 498.3 [M+H]$^+$ 100%.

HRMS (ES+): found 498.2384; required 498.2387 [M+H]$^+$.

Microanalysis calculated for C$_{30}$H$_{31}$N$_3$O$_4$×1.5H$_2$O

C, 68.68; H, 6.53; N, 8.01%. found C, 68.66; H, 6.35; N, 7.68%.

Example 46

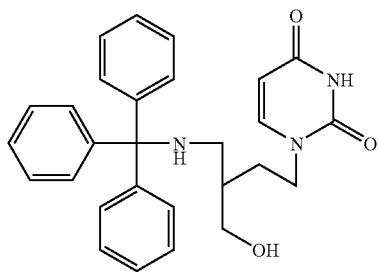

1-[3-Hydroxymethyl-4-(tritylamino)-butyl]-1H-pyrimidine-2,4-dione (46)

Compound (45) (110 mg, 0.22 mmol) was dissolved in 5 ml of a solution of MeONa in MeOH 0.2 M. The reaction was stirred at room temperature until TLC (DCM/MeOH 90:10) showed complete disappearance of the starting material. Then the solution was neutralized with Dowex H$^+$ resin. The polymer was filtered off, and the filtrate was concentrated and purified by filtration over a silica pad which gave the title compound as a white solid (100 mg, 99%). R: 0.66 in CHCl$_3$/MeOH 90:10

$^1$H-NMR (300 MHz, CDCl$_3$): δ 8.16 (bs; 1H; NH): 7.48-7.41 (m; 6H; H-14); 7.35-7.23 (m; 9H; H-15+H-16); 7.03 (d; J=7.91 Hz; 1H; H-6); 5.65 (d; J=7.90 Hz; 1H; H-5); 5.26 (bs; 2H; OH+NH); 3.95-3.90 (m; 1H; 1 of H-10); 3.82-3.57 (m; 3H; H-7+1 of H-10); 2.48-2.40 (m; 2H H-11); 1.84 (bs; 1H; H-9); 1.68-1.47 (m; 2H; H-8).

$^{13}$C-NMR (75 MHz, CDCl$_3$): δ 163.7 (C-4); 150.9 (C-2); 145.1 (C-13); 144.7 (C-6); 128.9 (C-14); 128.5 (C-15); 127.2 (C-16); 102.7 (C-s); 97.8 (C-12); 67.0 (C-10); 48.1 (C-11); 47.5 (C-7); 38.3 (C-9); 29.4 (C-8).

LRMS (CI+): m/z 456.3 [M+H]$^+$ 100%.

HRMS (ES+): found 456.2283; required 456.2282 [M+H]$^+$.

Microanalysis calculated for C$_{28}$H$_{29}$N$_3$O$_3$×1.0H$_2$O×HCl

C, 67.12; H, 6.24; N, 8.39%. found C, 67.15; H, 5.88; N, 8.16%.

Example 47

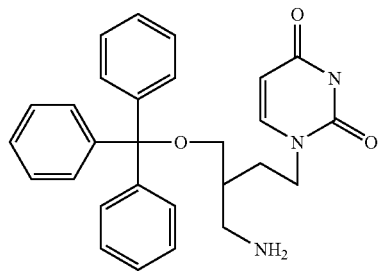

1-(3-Aminomethyl-4-trityloxybutyl)-1H-pyrimidine-2,4-dione (47)

TFA (2 ml) was added to a solution of compound 42 (100 mg, 0.18 mmol) in dichloromethane (4 ml) and the solution was stirred at room temperature. After 30 min the solvents were evaporated in vacuo and the afforded residue was purified by column chromatography on silica gel which gave the title compound (52 mg, 65%).

Example 48

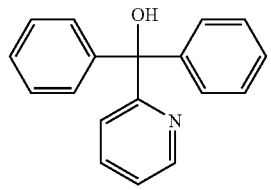

Diphenyl(pyridin-2-yl)methanol (48)

A solution of 2-bromopyridine (5 g, 0.032 mol) in dry THF (150 mL) was cooled to −70° C. To this cooled solution was added n-BuLi (2.8 M, 12.4 mL, 0.034 mol) over a period of 20 min and allowed to stir for 2 h under N$_2$ atmosphere. A solution of benzophenone (5.8 g, 0.032 mol) in dry THF (50 mL) was added to the solution at the same temperature over a period of 30 min. The reaction mixture was warmed slowly to RT and allowed to stir another 5 h at RT. The reaction mixture was concentrated under vacuum and the residue was washed with petrolieum ether. The organic layer was filtered and the filtrate was concentrated under vacuum to give the title compound (8 g, 95%).

Example 49

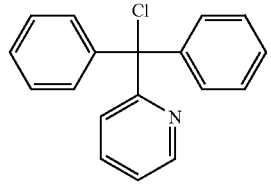

2-[Chloro(diphenyl)methyl]pyridine hydrochloride (49)

To a mixture of diphenyl(pyridin-2-yl)methanol (4 g, 0.015 mol) in thionylchloride (50 mL) was added acetylchloride (15 mL, 0.195 mol) at RT and heated to 50° C. for 48 h. The reaction mixture was concentrated under vacuum and the residue was azeotroped with dry benzene (100 mL×2) to give the title compound as the hydrochloride salt (4.4 g, >95%).

Example 50

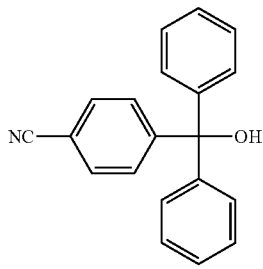

4-[Hydroxy(diphenyl)methyl]benzonitrile (50)

The procedure described in example 49 was followed but using 4-bromobenzonitrile (5 g, 0.027 mol) instead of 2-bromopyridine which gave the title compound (7.5 g, 94%).

Example 51

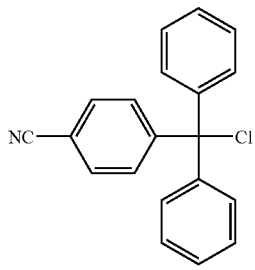

4-[Chloro(diphenyl)methyl]benzonitrile (51)

To a mixture of 4-[hydroxy(diphenyl)methyl] in dry toluene (60 mL) was added acetylchloride (3 mL) at RT and heated to 50° C. for 12 h. The reaction mixture was concentrated under vacuum. The residue was recrystallized from pet ether to give the product (1.7 g, 40%).

Example 52

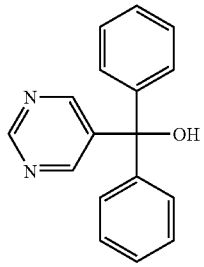

Diphenyl(pyrimidin-5-yl) methanol (52)

A solution of 5-bromopyrimidine (10 g, 0.063 mol) in a mixture of dry THF (150 mL) and hexane (50 mL) was cooled to −100° C. To this cooled solution was added n-BuLi (4 g, 21 mL, 0.062 mol) over a period of 30 min and stirred for another 30 min. A solution of benzophenone (11.5 g, 0.063 mol) in dry THF (50 mL) was added to this at the same temperature over a period of 30 min. The reaction mixture was warmed slowly to RT and allowed to stir another 1 h at RT. The reaction was quenched with cold water (200 mL), ethyl acetate was added and the organic layer was separated. The organic layer was dried, concentrated and the crude product was purified by column chromatography on silica gel (up-to 25% ethyl acetate in pet ether) to give the product (8 g). TLC: Pet. ether/EtOAc, 1:1, $R_f$=0.3

Example 53

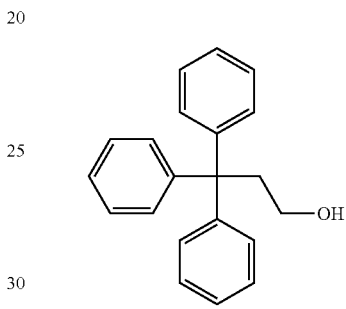

2,2,2-Triphenylethanol (53)

To a suspension of LAH (3.9 g, 0.104 mol) in dry THF (200 mL) was stirred at 0° C. for 20 min. A solution of 2,2,2-triphenylacetic acid (10 g, 0.034 mol) in dry THF (50 mL) was added in a drop-wise manner. The reaction mixture was stirred at RT overnight. Excess LAH was quenched with 1.5 N HCl and the reaction mixture was further stirred for 2 h at RT. The reaction mixture was filtered through celite, washed with ethyl acetate and the filtrate was concentrated under vacuum. The crude product was purified by column chromatography on silica gel (4% ethyl acetate in pet. ether) to give the title compound (4.6 g, 48%). TLC: Pet. ether/EtOAc, 7:3, $R_f$=0.2

Example 54

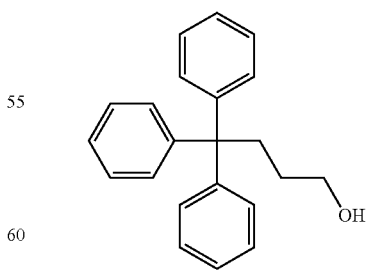

3,3,3-Triphenylpropan-1-ol (54)

To a magnetically stirred suspension of LAH (8.3 g, 0.219 mol) in dry THF (50 mL) was added a solution of 3,3,3- triphenylpropionic acid (9.5 g, 0.0314 mol) over a period of 30 min at 0° C. The reaction mixture was allowed to stir at RT for 14 h. The reaction mixture was cooled and excess LAH was quenched with 20% NaOH solution (50 mL). The reaction mixture was passed through celite, washed with THF and the filtrate was concentrated under vacuum. The residue was washed with pet ether and dried which gave the title compound (8 g, >85%).

TLC: Pet ether/EtOAc, 7:3, $R_f$=0.2

Example 55

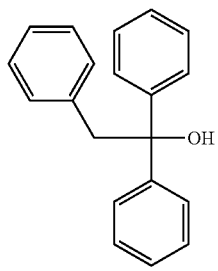

1,1,2-Triphenylethanol (55)

To a suspension of Mg (1.7 g, 0.07 mol) in dry ether (25 mL) was added a solution of benzyl bromide (10 mL, 1.5 equ.) in dry ether (25 mL) drop-wise and allowed to stir at RT for 1 h. By the time all magnesium was dissolved and the reaction mixture was cooled to 0° C. To this was added a solution of benzophenone (10 g, 0.05 mol) in dry ether (25 mL) and allowed to stir at RT for 5 h. The progress of the reaction was followed by TLC and when it was ready the reaction mixture was quenched with saturated NH$_4$Cl solution, extracted with ether (100 mL), washed with brine, dried and concentrated under vacuum. The crude product was purified by column chromatography on silica gel (10% ethyl acetate in pet. ether) to give the title compound (9.6 g, 65%) as a white solid. TLC: Pet. ether/EtOAc, 9:1, $R_f$=0.4

Example 56

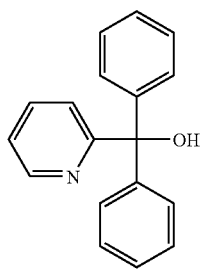

Diphenyl(pyridin-3-yl)methanol (56)

A solution of 3-bromopyridine (10 g, 0.063 mol) in dry THF (200 mL)/hexane (50 mL) was cooled to −90° C. To this cooled solution was added n-BuLi (2.2 M, 32 mL, 0.063 mol) slowly and allowed to stir for 30 min under N$_2$ atmosphere. A solution of benzophenone (11.5 g, 0.063 mol) in dry THF (50 mL) was added to this at the same temperature over a period of 30 min. The reaction mixture was warmed slowly to RT and allowed to stir another 3 h at RT. The reaction mixture was cooled, quenched with water (200 mL) and extracted with ethyl acetate (2×100 mL). The organic layer was dried, concentrated under vacuum and the crude product was purified by column chromatography on silica gel (30% ethyl acetate in pet. ether) which gave the title compound (3.3 g).

Biological Examples

Example B1

Malaria Whole Cell Assays

Parasite Cultures

Two strains of *P. falciparum* are used in this study: The drug sensitive NF54 (an airport strain of unknown origin) and K1 (Thailand, chloroquine and pyrimethamine resistant). The strains are maintained in RPMI-1640 medium with 0.36 mM hypoxanthine supplemented with 25 mM HEPES, 25 mM NaHCO$_3$, neomycin (100 U/ml) and Albumax® (lipid-rich bovine serum albumin) (GIBCO, Grand Island, N.Y.) (5 g/l), together with 5% washed human A+ erythrocytes. All cultures and assays are conducted at 37° C. under an atmosphere of 4% CO$_2$, 3% O$_2$ and 93% N$_2$. Cultures are kept in incubation chambers filled with the gas mixture. Subcultures are diluted to a parasitaemia of 0.1-0.5% and the medium changed daily.

Drug Sensitivity Assays

Antimalarial activity is assessed using an adaptation of the procedures described by Desjardins et al. (Antimicrob. Agents Chemother. 16(6):710-8, 1979), and Matile and Pink (In: Lefkovits, I. and Pernis, B. (Eds.). Immunological Methods. Academic Press, San Diego, pp. 221-234, 1990).

Stock drug solutions are prepared in 100% DMSO (dimethylsulfoxide) at 10 mg/ml, unless otherwise suggested by the supplier, and heated or sonicated if necessary. After use the stocks are kept at −20° C. The compound is further diluted to the appropriate concentration using complete medium without hypoxanthine.

Assays are performed in sterile 96-well microtiter plates, each well containing 200 μl of parasite culture (0.15% parasitemia, 2.5% hematocrit) with or without serial drug solutions. Seven 2-fold dilutions are used covering a range from 5 μg/ml to 0.078 μg/ml.

For active compounds the highest concentration is lowered (e.g. to 100 ng/ml), for plant extracts the highest concentration is increased to 50 μg/ml. Each drug is tested in duplicate and repeated once for active compounds showing an IC$_{50}$ below 0.5 μg/ml. After 48 hours of incubation at 37° C., 0.5 μCi $^3$H-hypoxanthine is added to each well. Cultures are incubated for a further 24 h before they are harvested onto glass-fiber filters and washed with distilled water. The radioactivity is counted using a Betaplate™ liquid scintillation counter (Wallac, Zurich, Switzerland). The results are recorded as counts per minute (CPM) per well at each drug concentration and expressed as percentage of the untreated controls. From the sigmoidal inhibition curves IC$_{50}$ values are calculated.

Primary Screen

K1 strain is used. The compounds are tested at 7 concentrations (5000 to 78 ng/ml). Artemisinin and chloroquine are included as reference drugs.

If the IC$_{50}$ is >5 μg/ml, the compound is classified as inactive

If the IC$_{50}$ is 0.5-5 µg/ml, the compound is classified as moderately active If the IC$_{50}$ is <0.5 µg/ml, the compound is classified as active and is further evaluated using two strains, K1 and NF54. A new range of concentrations is chosen depending on the IC$_{50}$ determined (e.g. 100 to 1.56 ng/ml) and the assay is carried out 2× independently.

The standard drugs are chloroquine and artemisinin which are run in the same assay. The IC$_{50}$ values for chloroquine are 2.9 ng/ml for NF54 and 48 ng/ml for K1; for artemisinin 1.9 ng/ml for NF54 and 0.8 ng/ml for K1.

Secondary Screen

Test compounds are tested against a panel of say, 14 different of different origin and some show resistances to chloroquine and/or pyrimethamine. If the range of the IC$_{50}$ values for the 14 strains is within a factor 3-5× then the tested compound is considered not to show cross resistance.

Example B2

Malaria Enzyme Assays

Inhibition of *Plasmodium falciparum* dUTPase

Chemicals

2'-dUTP, was purchased from Pharmacia. MgCl$_2$, BSA, and the pH indicator cresol red were from Sigma. The buffer N,N-bis(2-hydroxyethyl)glycine (BICINE) was obtained from USB (United States Biochemical), Ohio. All the concentrations of nucleotides were calculated spectrophotometrically (HP-8453, Hewlett Packard) at 280 nm, using the extinction coefficient ($\epsilon_{280\ nm}$=1.75 ml mg$^{-1}$cm$^{-1}$). Other chemicals used in these experiments were of the highest quality available.

Cloning of the PFdut Gene

Conserved motifs of the human dUTPase enzyme were used as query to identify the PFdut gene in the www.tigr.org database of the *Plasmodium falciparum* 3D7 strain. The entire coding sequence was amplified by the PCR using as template cDNA and as primers the oligonucleotides ATG-PFdut (CATATGCATTTAAAAATTGTATGTCTG) and TGA-PFdut (GGATCCTCAATATTTATTATCGATGTCGATC) which were designed so that NdeI and BamHI restriction sites were introduced at the 5 and 3' ends for convenient cloning in the expression vector pET11 (Stratagene). The amplified product was cloned into pGEMT (Promega) and propagated in *E. coli* XL1B cells. In order to confirm the correct sequence after amplification, sequencing was performed using an Applied Biosystems Automated Sequencer, at the Analytical Services of the Instituto de Parasitología y Biomedicina "López Neyra". These Services also supplied the oligonucleotides designed for the sequencing

*P. falciparum* dUTPase Overexpression and Purification

Recombinant *P. falciparum* dUTPase was purified from *E. coli* BL21 (DE3) cells transformed with pET-PFdut. Pellets from a liter of culture were resuspended in a solution consisting of buffer A (20 mM MES pH 5.5, 50 mM NaCl, 1 mM DTT) plus the protease inhibitors 1 mM PMSF, 20 µg/ml leupeptin and 1 mM benzamidine. Purification was carried out in a cold room (4° C.). The soluble crude extract was obtained by sonication in a Vibra-cell (Sonics and Materials Inc. Danbury, Conn., USA) and centrifugation at 14000×g. The extract was loaded onto a phosphocellulose column (Whatman) pre-equilibrated with buffer A at a flow rate of 1 mil/min. After washing the column with 100 ml of buffer A, elution was performed using a linear NaCl gradient of 50 to 1000 mM. Peak fractions with a low concentration of contaminating protein, as judged by 15% SDS-PAGE gels, were pooled and then loaded and chromatographed on a Superdex 200 column at a flow rate of 0.5 ml/min. The column was equilibrated with buffer B (50 mM Bicine, 1 mM DTT, 10 mM MgCl$_2$). Peak fractions were pooled and concentrated to about 5 mg/ml by ultrafiltration in a Centripep tube (Amicon) and stored at −80° C.

Kinetic Measurements

Nucleotide hydrolysis was monitored by mixing enzyme and substrate with a rapid kinetic accessory (Hi-Tech Scientific) attached to a spectrophotometer (Cary 50) and connected to a computer for data acquisition and storage. Protons, released through the hydrolysis of nucleotides, were neutralised by a pH indicator in a weak buffered medium with similar pK$_a$ and monitored spectrophotometrically at the absorbance peak of the basic form of the indicator. Absorbance changes were kept within 0.1 units. The indicator/buffer pair used was cresol red/BICINE (2 mM/50 µM, pH 8, 573 nm). The measurements were performed at 25° C., and the solutions were previously degassed. Assays contained 30 nM purified recombinant enzyme, 50 µM dUTP, 5 mM MgCl$_2$ and 2.5 mM DTT, 1.25 mg/ml BSA and 100 mM KCl. Indicator absorbance changes corresponding to complete hydrolysis of nucleotides were recorded in the computer, and the kinetic parameters V$_{max}$ and K$_{mapp}$ (or slope) were calculated by fitting the data to the integrated Michaelis-Menten equation (Segel, 1975).

$$[dUMP]/t = V_{max} - K_{map}/t \ln [dUTP]/([dUTP]-[dUMP])$$

Solutions of potential inhibitors were prepared at 10 mg/ml and tested routinely at concentrations of 2, 10, and 50 µg/µl. A wider range of concentrations was further tested when necessary for K$_i$ determination. The different apparent K$_m$ values attained were plotted against inhibitor concentration and K$_i$ values were obtained according to the following equation:

$$K_{map} = \frac{K_m}{K_I}[I] + K_m$$

Example B3

Human dUTPase Assay

Human recombinant dUTPase was purified from *E. coli* BL21 (DE3) cells transformed with pETHudut (Dr. P. O. Nyman, Lund University). Purification was accomplished as described for the dUTPase above except that the last step in Superdex 200 was omitted. Likewise, conditions for enzyme assays were the same as described above except that the enzyme concentration was 50 nM.

Example B4

*Trypanosoma brucei* Whole Cell Assays

Parasite Cultures

Three strains of *T. brucei* spp. are used in this study: (a) *Trypanosomal brucei rhodesiense* STIB 900, a clone of a population isolated in 1982 from a patient in Tanzania which is known to be susceptible to all currently used drugs; (b) *Trypanosoma bruncei gambiense* STIB 930, a derivative of strain TH1/78E (031) isolated in 1978 from a patient in Ivory Coast which is known to be sensitive to all drugs used, and (c) *Trypanosoma brucei brucei* STIB 950, a clone of a population isolated in 1985 from a bovine in Somalia which shows drug resistance to diminazene, isometamidium and quinapyramine.

The bloodstream form trypomastigotes of the strains a and c are maintained in MEM medium with Earle's salts supplemented with 25 mM HEPES, 1 g/l additional glucose, 1% MEM non-essential amino acids (100×), 0.2 mM 2-mercaptoethanol, 2 mM Na-pyruvate, 0.1 mM hypoxanthine and 15% heat inactivated horse serum.

The bloodstream form trypomastigotes of strain b are maintained in MEM medium with Earle's salts supplemented with 25 mM HEPES, 1 g/l additional glucose, 1% MEM non-essential aminoacids (100×), 0.2 mM 2-mercaptoethanol, 2 mM Na-pyruvate, 0.1 mM hypoxanthine, 0.05 mM bathocuproine disulphonic acid, 0.15 mM L-cysteine and 15% heat inactivated pooled human serum.

All cultures and assays are conducted at 37° C. under an atmosphere of 5% $CO_2$ in air.

Drug Sensitivity Assays

Stock drug solutions are prepared in 100% DMSO (unless otherwise suggested by the supplier) at 10 mg/ml, and heated or sonicated if necessary. After use the stocks are kept at −20° C. For the assays, the compound is further diluted to the appropriate concentration using complete medium.

Assays are performed in 96-well microtiter plates, each well containing 100 μl of culture medium with 8×10³ bloodstream forms with or without a serial drug dilution. The highest concentration for the test compounds is 90 μg/ml. Seven 3-fold dilutions are used covering a range from 90 μg/ml to 0.123 μg/ml. Each drug is tested in duplicate and each assay is repeated at least once. After 72 hrs of incubation the plates are inspected under an inverted microscope to assure growth of the controls and sterile conditions.

10 μl of Alamar Blue (12.5 mg resazurin dissolved in 100 ml distilled water) are now added to each well and the plates incubated for another 2 hours. Then the plates are read with a Spectramax Gemini XS microplate fluorometer (Molecular Devices Cooperation, Sunnyvale, Calif., USA) using an excitation wave length of 536 nm and an emission wave length of 588 nm. Data are analysed using the microplate reader software Softmax Pro (Molecular Devices Cooperation, Sunnyvale, Calif., USA).

Primary Screen

The preliminary screen uses the *Trypanosoma b. rhodesiense* strain. The compounds are tested at 7 concentrations (drug concentrations ranging from 90 μg/ml to 0.123 μg/ml in 3-fold dilutions).

If the $IC_{50}$ is >3 μg/ml, the compound is classified as inactive

If the $IC_{50}$ is 0.2-3 μg/ml, the compound is classified as moderately active If the $IC_{50}$ is <0.2 μg/ml, the compound is classified as active The standard drug is melarsoprol which is run in the same assay; the $IC_{50}$ for melarsoprol is 1.6 ng/ml.

Secondary Screen

Active compounds ($IC_{50}$<0.2 μg/ml) are tested against the *Trypanosoma brucei gambiense* STIB 930 and the drug resistant *T. b. brucei* STIB 950 following the same protocol as described above.

The standard drug is melarsoprol which is run in the same assay; the $IC_{50}$ for melarsoprol is 4.2 ng/ml for STIB 930 and 2.8 ng/ml for STIB 950

Example B5

*Trypanosoma cruzi* Whole Cell Assays

*Trypanosoma cruzi* Cell Cultures:

The *Trypanosoma cruzi* Tulahuen C2C4 strain, containing the galactosidase (Lac Z) gene, is used. The plasmid construct by Dr. S. Reed was obtained from Dr. F. Buckner, Seattle, as epimastigotes in LIT medium.

The infective amastigote and trypomastigote stages are cultivated in L-6 cells (rat skeletal myoblast cell line) in RPMI 1640 supplemented with 2 mM L-glutamine and 10% heat-inactivated foetal bovine serum in 12.5 $cm^2$ tissue culture flasks. Amastigotes develop intracellularly, differentiate into trypomastigotes and leave the host cell. These trypomastigotes infect new L-6 cells and are the stages used to initiate an infection in the assay. All cultures and assays are conducted at 37° C. under an atmosphere of 5% $CO_2$ in air.

Drug Sensitivity Assays

Stock drug solutions are prepared in 100% DMSO (dimethylsulfoxide) unless otherwise suggested by the supplier at 10 mg/ml, and heated or sonicated if necessary. The stocks are kept at −20° C. For the assays, the compound is further diluted to the appropriate concentration using complete medium.

Assays are performed in sterile 96-well microtiter plates, each well containing 100 μl medium with 2×10³ L-6 cells. After 24 hours 50 μl of a trypanosome suspension containing 5×10³ trypomastigote bloodstream forms from culture are added to the wells. 48 hours later the medium is removed from the wells and replaced by 100 μl fresh medium with or without a serial drug dilution. At this point the L-6 cells should be infected with amastigotes and no free trypomastigotes should be in the medium. Seven 3-fold dilutions are used covering a range from 90 μg/ml to 0.123 μg/ml. Each drug is tested in duplicate. After 96 hours of incubation the plates are inspected under an inverted microscope to assure growth of the controls and sterility.

Then the substrate CPRG/Nonidet (50 l) is added to all wells. A colour reaction will become visible within 2-6 hours and can be read photometrically at 540 nm. Data are transferred into a graphic programme (e.g. EXCEL), sigmoidal Inhibition curves determined and $IC_{50}$ values calculated.

Primary Screen

Benznidazole is used as the reference drug and shows an $IC_{50}$ value of 0.34 μg/ml.

If the $IC_{50}$ is >30 μg/ml, the compound is classified as inactive.

If the $IC_{50}$ is between 2 and 30 μg/ml, the compound is classified as moderately active.

If the $IC_{50}$ is <2 μg/ml, the compound is classified as active.

Example B6

Leishmaniasis

Macrophage In Vitro Screening Model

Parasite and Cell Cultures

The *Leishmania. donovani* strain MHOM/ET/67/L82 obtained from Dr. S. Croft, London) is used. The strain is maintained in the Syrian Golden hamster. Amastigotes are collected from the spleen of an infected hamster Amastigotes are grown in axenic culture at 37° C. in SM medium (Cunningham I., J. Protozool. 24, 325-329, 1977) at pH 5.4 supplemented with 10% heat-inactivated foetal bovine serum under an atmosphere of 5% $CO_2$ in air.

Primary peritoneal macrophages from NMRI mice are collected 1 day after a macrophage production stimulation with an i.p injection of 2 ml of a 2% potato starch suspension (FLUKA, Switzerland) All cultures and assays are done at 37° C. under an atmosphere of 5% $CO_2$ in air.

Drug Sensitivity Assays

Stock drug solutions are prepared in 100% DMSO (unless otherwise suggested by the supplier) at 10 mg/ml, and heated or sonicated if necessary. After use the stocks are kept at –20° C. For the assays, the compound is further diluted in serum-free culture medium and finally to the appropriate concentration in complete medium.

Assays are performed in sterile 16-well chamber slides (LabTek, Nalgene/Nunc Int.) To each well 100 μl of a murine macrophage suspension ($4 \times 10^5$/ml) in RPMI 1640 (containing bicarbonate and HEPES) supplemented with 10% heat inactivated fetal bovine serum is added. After 24 hrs 100 μl of a suspension containing amastigotes ($1.2 \times 10^6$/ml) is added resulting in a 3:1 ratio of amastigotes/macrophages. The amastigotes are harvested from an axenic amastigote culture and suspended in RPMI/FBS. 24 hrs later, the medium containing free amastigotes is removed, washed 1× and replaced by fresh medium containing four 3-fold drug dilutions. In this way 4 compounds can be tested on one 16-well tissue culture slide. Untreated wells serve as controls. Parasite growth in the presence of the drug is compared to control wells. After 4 days of incubation the culture medium is removed and the slides fixed with methanol for 10 min followed by staining with a 10% Giemsa solution. Infected and non-infected macrophages are counted for the control cultures and the ones exposed to the serial drug dilutions. The infection rates are determined. The results are expressed as % reduction in parasite burden compared to control wells, and the $IC_{50}$ calculated by linear regression analysis.

Primary Screen

The compounds are tested in duplicate at 4 concentrations ranging from 9 to 0.3 μg/m. If the $IC_{50}$ is below 0.3 μg/ml then the range is changed to 1 to 0.03 μg/ml. Miltefosine is used as the reference drug and shows an $IC_{50}$ value of 0.325 μg/ml (0.22-0.42 μg/ml; n=4)

If the $IC_{50}$ is higher than 10 μg/ml, the compound is classified as inactive.

If the $IC_{50}$ is between 2 and 10 μg/ml, the compound is classified as moderately active.

If the $IC_{50}$ is <2 μg/ml, the compound is classified as active and is further evaluated in a secondary screening.

Drug Sensitivity Assays

Stock drug solutions are prepared in 100% DMSO (dimethylsulfoxide) unless otherwise suggested by the supplier at 10 mg/ml, and heated or sonicated if necessary. The stocks are kept at –20° C. For the assays, the compound is further diluted to the appropriate concentration using complete medium.

Assays are performed in sterile 96-well microtiter plates, each well containing 100 μl medium with $2 \times 10^3$ L-6 cells. After 24 hours 50 μl of a trypanosome suspension containing $5 \times 10^3$ trypomastigote bloodstream forms from culture are added to the wells. 48 hours later the medium is removed from the wells and replaced by 100 μl fresh medium with or without a serial drug dilution. At this point the L-6 cells should be infected with amastigotes and no free trypomastigotes should be in the medium. Seven 3-fold dilutions are used covering a range from 90 μg/ml to 0.123 μg/ml. Each drug is tested in duplicate. After 96 hours of incubation the plates are inspected under an inverted microscope to assure growth of the controls and sterility.

Then the substrate CPRG/Nonidet (50 μl) is added to all wells. A colour reaction will become visible within 2-6 hours and can be read photometrically at 540 nm. Data are transferred into a graphic programme (e.g. EXCEL), sigmoidal inhibition curves determined and $IC_{50}$ values calculated.

Primary Screen

Benznidazole is used as the reference drug and shows an $IC_{50}$ value of 0.34 μg/ml.

If the $IC_{50}$ is >30 μg/ml, the compound is classified as inactive.

If the $IC_{50}$ is between 2 and 30 μg/ml, the compound is classified as moderately active.

If the $IC_{50}$ is <2 μg/ml, the compound is classified as active.

Example B7

*Leishmania donovani*, Axenic Amastigote Assay

Parasite and Cell Cultures:

The *Leishmania donovani* strain MHOM/ET/67/L82) is used. The strain is maintained in the hamster. Amastigotes are collected from the spleen of an infected hamster and adapted to axenic culture conditions at 37° C. The medium is a 1:1 mixture of SM medium (Cunningham I., J. Protozool. 24, 325-329, 1977) and SDM-79 medium (Brun, R. & Schönenberger, M., Acta Trop. 36, 289-292, 1979) at pH 5.4 supplemented with 10% heat-inactivated FBS under an atmosphere of 5% $CO_2$ in air.

Drug Sensitivity Assays

Stock drug solutions are prepared in 100% DMSO (unless otherwise suggested by the supplier) at 10 mg/ml, and heated or sonicated if necessary. After use the stocks are kept at –20° C. For the assays, the compound is further diluted to the appropriate concentration using complete medium.

Assays are performed in 96-well microtiter plates, each well containing 100 pt of culture medium with $10^5$ amastigotes from axecic culture with or without a serial drug dilution. The highest concentration for the test compounds is 90 μg/ml. Seven 3-fold dilutions are used covering a range from 30 μg/ml to 0.041 μg/ml. Each drug is tested in duplicate and each assay is repeated at least once. After 72 hours of incubation the plates are inspected under an inverted microscope to assure growth of the controls and sterile conditions.

10 μl of Alamar Blue (12.5 mg resazurin dissolved in 1 L distilled water) are now added to each well and the plates incubated for another 2 hours. Then the plates are read with a Spectramax Gemini XS microplate fluorometer (Molecular Devices Cooperation, Sunnyvale, Calif., USA) using an excitation wave length of 536 nm and an emission wave length of 588 nm.

Data are analysed using the microplate reader software Softmax Pro (Molecular Devices Cooperation, Sunnyvale, Calif., USA).

Primary Screen

The compounds are tested in duplicate at 7 concentrations. Miltefosine is used as the reference drug and shows an $IC_{50}$ value of 0.12 μg/ml.

If the $IC_{50}$ is >3 μg/ml, the compound is classified as inactive

If the IC$_{50}$ is 0.1-3 µg/ml, the compound is classified as moderately active If the IC$_{50}$ is <0.1 µg/ml, the compound is classified as active Secondary Screen Active and moderately active compounds are tested in the macrophage assay with intracellular amastigotes in their host cells, murine macrophages.

Example B8

Biological Results

Compounds of the invention, such as those in the examples above, typically show activities in the low micromolar range for *Plasmodium falciparum* enzyme (K$_i$) and cell culture (ED$_{50}$), with selectivity (SI) over the human enzyme of at least 10-fold.

| | Ki uM | SI | ED$_{50uM}$ |
|---|---|---|---|
| | 0.9 | 1111 | 3.8 |
| | 4.29 | >233 | 2.2 |
| | 0.67 | 25.3 | 0.9 |
| | 1.62 | 617 | 4.9 |

| | Ki uM | SI | ED$_{50uM}$ |
|---|---|---|---|
| 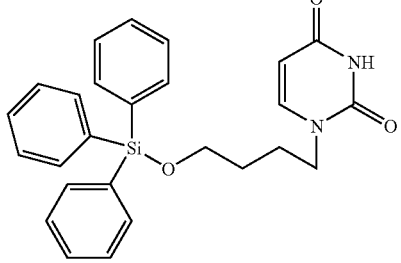 | 1.69 | 226 | 0.43 |

ABBREVIATIONS

| DMF | dimethylformamide |
|---|---|
| RT | room temperature |
| Ac | acetyl |
| LAH | lithiumaluminiumhydride |
| DMAP | dimethylaminopyridine |
| DCM | dichloromethane |
| THF | tetrahydrofuran |
| TEA | triethylamine |
| TLC | thin layer chromatography |
| EtOAc | ethyl acetate |

Throughout the specification and the claims which follow, unless the context requires otherwise, the word 'comprise', and variations such as 'comprises' and 'comprising', will be understood to imply the inclusion of a stated integer, step, group of Integers or group of steps but not to the exclusion of any other integer, step, group of integers or group of steps.

The invention claimed is:

1. A method for the treatment of parasitic infections that cause malaria in man or a zoonose vector comprising the administration of an effective amount of a compound of formula I to a patient in need thereof, or to the vector:

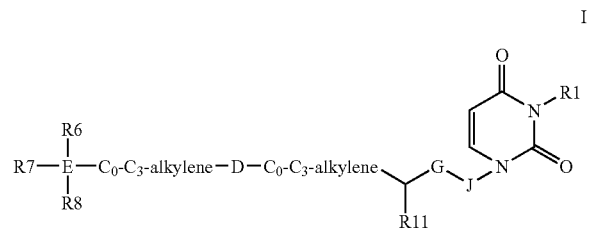

where $R^1$ is H, $C_1$-$C_5$ alkyl, $C_2$-$C_5$ alkenyl, $C_2$-$C_5$ alkynyl or a 5 or 6 membered, saturated or unsaturated ring containing 0 to 3 heteroatoms selected from N O and S, the alkyl, alkenyl, alkynyl or ring being independently optionally substituted with $R^4$;

D is —NHCO—, —CONH—, —O—, —C(=O)—, —CH=CH—, —C≡C—, —NR$^5$—;

$R^4$ is hydrogen, halo, cyano, amino, nitro, carboxy, carbamoyl, hydroxy, oxo, $C_1$-$C_5$ alkyl, $C_1$-$C_5$ haloalkyl, $C_1$-$C_5$ alkyloxy, $C_1$-$C_5$ alkanoyl, $C_1$-$C_5$ alkanoyloxy, $C_1$-$C_5$ alkylthio, —N($C_0$-$C_3$-alkyl)$_2$, hydroxymethyl, aminomethyl, carboxymethyl; —SO$_2$N($C_0$-$C_3$-alkyl), —SO$_2$C$_1$-C$_5$-alkyl;

$R^5$ is H, $C_1$-$C_4$ alkyl, $C_1$-$C_4$ alkanoyl;

E is Si or C;

$R^6$, $R^7$ and $R^8$ are independently selected from $C_1$-$C_8$ alkyl, $C_2$-$C_8$ alkenyl, $C_2$-$C_8$ alkynyl or a stable monocyclic, bicyclic or tricyclic ring system which is saturated or unsaturated in which each ring has 0 to 3 heteroatoms selected from N, O and S, $R^6$, $R^7$ and $R^8$ are independently optionally substituted with $R^4$;

G is —O—, —S—, —CHR$^{10}$—, —C(=O)—;

J is —CH$_2$—, or when G is CHR$^{10}$ may also be —O— or —NH—;

$R^{10}$ is H, F, —CH$_3$, —CH$_2$NH$_2$, —CH$_2$OH, —OH; or a pharmaceutically acceptable ether, ester or amide created through reaction of the preceding hydroxyl and/or amino group;

$R^{11}$ is H, F, —CH$_3$, —CH$_2$NH$_2$, —CH$_2$OH, CH(OH)CH$_3$, CH(NH$_2$)CH$_3$; or a pharmaceutically acceptable ether, ester or amide created through reaction of the preceding hydroxyl and/or amino group; or $R^{10}$ and $R^{11}$ together define an olefinic bond, or together form a —CH$_2$-group, thereby defining a cis or trans cyclopropyl group;

and pharmaceutically acceptable salts thereof.

2. The method according to claim 1, wherein G is —O— or —CH$_2$—.

3. The method according to claim 1 wherein $R^{10}$ and $R^{11}$ define an olefinic bond or a cyclopropyl group.

4. The method according to claim 1, wherein $R^{11}$ is H; CH$_2$OH or a pharmaceutically acceptable ether or ester thereof; or CH$_2$NH$_2$ or a pharmaceutically acceptable amide thereof.

5. The method according to claim 1, wherein $R^1$ is H.

6. The method according to claim 1, wherein D is —O— or —NH—.

7. The method according to claim 6, wherein $C_0$-$C_3$-alkylene-D-$C_0$-$C_3$-alkylene is oxymethylene, oxyethylene or oxypropylene.

8. The method according to claim 6, wherein $C_0$-$C_3$-alkylene-D-$C_0$-$C_3$-alkylene is aminomethylene, aminoethylene or aminopropylene.

9. The method according to claim 1, wherein at least two of $R^6$, $R^7$ and $R^8$ are aryl.

10. The method according to claim 1, wherein $R^6$ is optionally substituted phenyl.

11. The method according to claim 10 wherein $R^8$ is optionally substituted phenyl or pyridyl.

12. The method according to claim 1 wherein E is C.

13. The method according to any preceding claim, wherein the zoonose vector is a parasite and a *Plasmodium* species.

* * * * *